US012728113B2

(12) United States Patent
Zhu et al.

(10) Patent No.: US 12,728,113 B2
(45) Date of Patent: Sep. 8, 2026

(54) MICROSUSPENSION OF AN MDM2 INHIBITOR AND THERAPEUTIC APPLICATIONS THEREOF

(71) Applicants: ASCENTAGE PHARMA (SUZHOU) CO., LTD., Suzhou (CN); ASCENTAGE PHARMA GROUP CORP LIMITED, Central (CN)

(72) Inventors: Saijie Zhu, Suzhou (CN); Douglas Dong Fang, Suzhou (CN); Yifan Zhai, Suzhou (CN); Dajun Yang, Suzhou (CN)

(73) Assignees: Ascentage Pharma (Suzhou) Co., Ltd. (CN); Ascentage Pharma Group Corp Limited (CN)

( * ) Notice: Subject to any disclaimer, the term of this patent is extended or adjusted under 35 U.S.C. 154(b) by 763 days.

(21) Appl. No.: 18/001,500

(22) PCT Filed: Jun. 11, 2021

(86) PCT No.: PCT/CN2021/099808
§ 371 (c)(1),
(2) Date: Dec. 12, 2022

(87) PCT Pub. No.: WO2021/254277
PCT Pub. Date: Dec. 23, 2021

(65) Prior Publication Data

US 2023/0218575 A1 Jul. 13, 2023

(30) Foreign Application Priority Data

Jun. 25, 2020 (WO) ................ PCT/CN2020/096143

(51) Int. Cl.

| | |
|---|---|
| ***A61K 31/407*** | (2006.01) |
| ***A61K 9/14*** | (2006.01) |
| ***A61K 47/26*** | (2006.01) |
| ***A61K 47/34*** | (2017.01) |

(52) U.S. Cl.
CPC .............. *A61K 31/407* (2013.01); *A61K 9/14* (2013.01); *A61K 47/26* (2013.01); *A61K 47/34* (2013.01)

(58) Field of Classification Search
CPC .................................................... A61K 31/407
See application file for complete search history.

(56) References Cited

FOREIGN PATENT DOCUMENTS

| | | | |
|---|---|---|---|
| CN | 109843329 | A | 6/2019 |
| WO | WO2012047587 | A2 | 4/2012 |
| WO | WO2015070224 | A2 | 5/2015 |
| WO | WO2015161032 | A1 | 10/2015 |
| WO | WO2020030016 | A1 | 2/2020 |
| WO | WO2020103922 | A1 | 5/2020 |
| WO | WO2021018032 | A1 | 2/2021 |

OTHER PUBLICATIONS

Blanco-Marchite, C., et al., IVOS, 2011, 52(11), 8467-8478 (Year: 2011).*

Moritz, M.L., Pediatric Nephrology, pub. Sep. 2018, 34, 1299-1300 (Year: 2018).*

Aug. 26, 2021 PCT ISR & Written Opinion for PCT/CN2021/099808, 16 pages.

* cited by examiner

*Primary Examiner* — John S Kenyon
*Assistant Examiner* — Sara Elizabeth Bell
(74) *Attorney, Agent, or Firm* — Honigman LLP; Lucy Yang; Li Gao

(57) ABSTRACT

Provided herein is a microsuspension of an MDM2 inhibitor, comprising microparticles of the MDM2 inhibitor, e.g., a compound of Formula (I), a surfactant, and a tonicity agent. Also provided herein is a method of treating an MDM2-mediated disorder, disease, or condition with the microsuspension.

18 Claims, 1 Drawing Sheet

MICROSUSPENSION OF AN MDM2 INHIBITOR AND THERAPEUTIC APPLICATIONS THEREOF

CROSS-REFERENCE TO RELATED APPLICATIONS

This application is a 35 U.S.C. § 371 United States National Phase Application of, and claims priority to, PCT Application No. PCT/CN2021/099808, filed Jun. 11, 2021, which claims priority to Application No. PCT/CN2020/096143, filed Jun. 15, 2020. The entire contents of the aforementioned applications are incorporated herein by reference.

FIELD

Provided herein is a microsuspension of an MDM2 inhibitor, comprising microparticles of the MDM2 inhibitor, a surfactant, and a tonicity agent. Also provided herein is a method of treating an MDM2-mediated disorder, disease, or condition with the microsuspension.

BACKGROUND

The p53 tumor suppressor is a key transcription factor that controls the life and death of a cell. Vousden & Lu, *Nat. Rev Cancer* 2002, 2, 594-604. It acts as an important defense mechanism against cancer onset and progression. Nag et al., *J. Biomed. Res.* 2013, 27, 254-271. As the cellular gatekeeper, p53 is activated in response to oncogenic stress stimuli, resulting in the inhibition of tumor-cell growth. Balint & Vousden, *Br. J. Cancer* 2001, 85, 1813-1823. However, the tumor-suppression function of p53 is compromised in almost all human cancer. Issaeva, *Cancers* (*Basel*) 2019, 11, E332; Kocik et al., *Cancers* (*Basel*) 2019, 11, E1014. In about half of all human cancer, the p53 is inactivated by loss-of-function mutations/deletions in the TP53 gene encoding p53. Kocik et al., *Cancers* (*Basel*) 2019, 11, E1014. In the remaining cancer, p53 function is inhibited primarily by the murine double minute 2 (MDM2) protein via a direct protein-protein interaction. Shangary et al., *Clin. Cancer Res.* 2008, 14, 5318-4324.

MDM2 is a primary negative regulator of p53. Kubbutat et al., *Nature* 1997, 387, 299-303; Shi and Gu, Genes *Cancer* 2012, 3, 240-248. In the absence of stress, MDM2 binds to the transactivation domain of p53, preventing it from binding to DNA and marking it for proteasomal degradation. Id. In this way, MDM2-p53 interaction limits p53 abundance and p53-mediated tumor-suppressor functions. Id. Aberrant MDM2 expression restricts p53 and its tumor-suppressor functions, leaving cells more susceptible to oncogenic mutations, transformation, and subsequent tumor growth. Oliner et al., *Nature* 1993, 362, 857-860; Kussie et al., *Science* 1996, 274, 948-953; Bond et al., *Cell* 2004, 119, 591-602; Oliner et al., *Cold Spring Harb. Perspect. Med.* 2016, 6, a026336. Preclinical data have shown that blocking MDM2-p53 interactions by a small molecule MDM2 inhibitor induce apoptosis in both MDM2-overexpressing and wild-type tumor cell lines, thus demonstrating that small molecule inhibitors designed to block the MDM2-p53 interaction can liberate the tumor suppressor function of wild-type p53. Vassilev, *Trends Mol. Med.* 2007, 13, 23-31; Vu & Vassilev, *Curr. Top. Microbiol. Immunol.* 2011, 348, 151-172; Chen et al., *Oncotarget* 2017, 8, 43008-43022; Aguilar et al., *J. Med. Chem.* 2017, 60, 2819-2839.

Despite the advances in cancer treatment, cancer remains a major worldwide public health problem. It was estimated that there will be 1,762,450 new cancer cases diagnosed and 606,880 cancer deaths in the US alone in 2019. *Cancer Facts & Figures.* 2019. Therefore, there is still a need for an effective therapy for an MDM2-mediated disorder, disease or condition, such as cancer.

SUMMARY OF THE DISCLOSURE

Provided herein is a microsuspension of an MDM2 inhibitor, comprising: (i) microparticles of the MDM2 inhibitor; (ii) a surfactant; and (iii) a tonicity agent; wherein the MDM2 inhibitor is a compound of Formula (I):

(I)

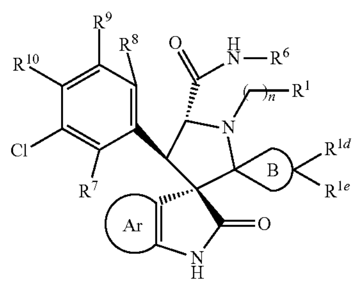

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

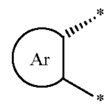

is

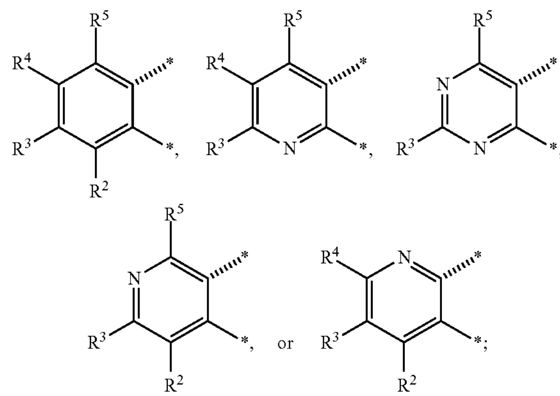

ring B is $C_{3-10}$ cycloalkyl or heterocyclyl;

$R^1$ is hydrogen, $C_{1-6}$ alkyl, $C_{3-10}$ cycloalkyl, heterocyclyl, $-NR^{1b}R^{1c}$, or $-OR^{1a}$;

n is an integer of 0, 1, or 2;

$R^2$, $R^3$, $R^4$, $R^5$, $R^7$, $R^8$, $R^9$, and $R^{10}$ are each independently hydrogen, fluoro, chloro, methyl, or trifluoromethyl;

$R^6$ is

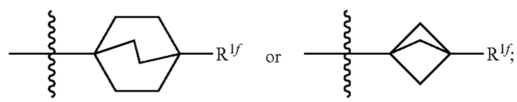

wherein each $R^{1f}$ is independently —C(═O)O$R^{1a}$, —C(═O)N$R^{1b}R^{1c}$, or —C(═O)NH$SO_2CH_3$;

$R^{1d}$ and $R^{1e}$ are each independently hydrogen, halo, $C_{1-6}$ alkyl, or —O$R^{1a}$; or $R^{1d}$ and $R^{1e}$ together with the carbon to which they are attached form $C_{3-10}$ cycloalkyl or heterocyclyl; and each $R^{1a}$, $R^{1b}$, and $R^{1c}$ is independently hydrogen or $C_{1-6}$ alkyl;

wherein each alkyl, cycloalkyl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(═N$R^a$)N$R^bR^c$, —OC(S)$R^a$, —OC(S)O$R^a$, —OC(S)N$R^bR^c$, —OS(O)$R^a$, —OS$(O)_2R^a$, —OS(O)N$R^bR^c$, —OS$(O)_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(═N$R^d$)N$R^bR^c$, —N$R^a$C(S)$R^d$, —N$R^a$C(S)O$R^d$, —N$R^a$C(S)N$R^bR^c$, —N$R^a$S(O)$R^d$, —N$R^a$S$(O)_2R^d$, —N$R^a$S(O)N$R^bR^c$, —N$R^a$S$(O)_2$N$R^bR^c$, —S$R^a$, —S(O)$R^a$, —S$(O)_2R^a$, —S(O)N$R^bR^c$, and —S$(O)_2$N$R^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(O)S$R^e$, —C(N$R^e$)N$R^fR^g$, —C(S)$R^e$, —C(S)O$R^e$, —C(S)N$R^fR^g$, —O$R^e$, —OC(O)$R^e$, —OC(O)O$R^e$, —OC(O)N$R^fR^g$, —OC(O)S$R^e$, —OC(═N$R^e$)N$R^fR^g$, —OC(S)$R^e$, —OC(S)O$R^e$, —OC(S)N$R^fR^g$, —OS(O)$R^e$, —OS$(O)_2R^e$, —OS(O)N$R^fR^g$, —OS$(O)_2$N$R^fR^g$, —N$R^fR^g$, —N$R^e$C(O)$R^h$, —N$R^e$C(O)O$R^f$, —N$R^e$C(O)N$R^fR^g$, —N$R^e$C(O)S$R^f$, —N$R^e$C(═N$R^h$)N$R^fR^g$, —N$R^e$C(S)$R^h$, —N$R^e$C(S)O$R^f$, —NR C(S)N$R^fR^g$, —N$R^e$S(O)$R^h$, —N$R^e$S$(O)_2R^h$, —N$R^e$S(O)N$R^fR^g$, —N$R^a$S$(O)_2$N$R^fR^g$, —S$R^e$, —S(O)$R^e$, —S$(O)_2R^e$, —S(O)N$R^fR^g$, and —S$(O)_2$N$R^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Also provided herein is a method of treating, preventing, or alleviating one or more symptoms of a disorder, disease, or condition mediated by an MDM2 in a subject, comprising administering to the subject in need thereof a therapeutically effective amount of an microsuspension provided herein.

DETAILED DESCRIPTION

Figure 1:
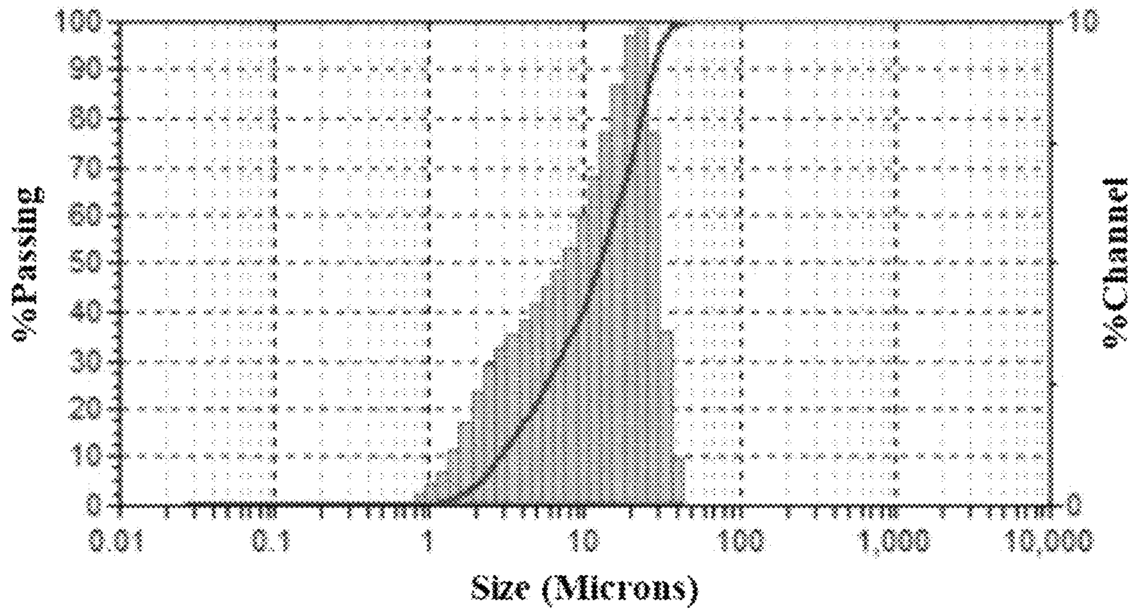
FIG. 1 shows the particle size distribution of microsuspension 1.

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, e.g., *Remington: The Science and Practice of Pharmacy,* 22nd ed.; Allen Ed.: Philadelphia, PA, 2012*; Handbook of Pharmaceutical Excipients,* 8th ed.; Sheskey et al., Eds.; The Pharmaceutical Press: 2017*; Handbook of Pharmaceutical Additives,* 3rd ed.; Ash and Ash Eds.; Gower Publishing Company: 2007*; Pharmaceutical Preformulation and Formulation,* 2nd ed.; Gibson Ed.; CRC Press LLC: Boca Raton, FL, 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "alkyl" refers to a linear or branched saturated monovalent hydrocarbon radical, wherein the alkyl is optionally substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkenyl" refers to a linear or branched monovalent hydrocarbon radical, which contains one or more, in one embodiment, one, two, three, four, or five, in another embodiment, one, carbon-carbon double bond(s). The alkenyl is optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one, two, three, four, or five, in another embodiment, one, carbon-carbon triple bond(s). The alkynyl is optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 4 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 4 to 20 ($C_{4-20}$), 4 to 15 ($C_{4-15}$), 4 to 10 ($C_{4-10}$), or 4 to 6 ($C_{4-6}$) carbon atoms. Examples of alkynyl groups include, but are not limited to, ethynyl ($-C\equiv CH$), propynyl (including all isomeric forms, e.g., 1-propynyl ($-C\equiv CCH_3$) and propargyl ($-CH_2C\equiv CH$)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "cycloalkyl" refers to a cyclic monovalent hydrocarbon radical, which is optionally substituted with one or more substituents Q as described herein. In one embodiment, the cycloalkyl is a saturated or unsaturated but non-aromatic, and/or bridged or non-bridged, and/or fused bicyclic group. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. In one embodiment, the cycloalkyl is monocyclic. In another embodiment, the cycloalkyl is bicyclic. In yet another embodiment, the cycloalkyl is polycyclic. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[1.1.1]pentyl, bicyclo[2.1.1]hexyl, bicyclo[2.2.1]heptyl, bicyclo[2.2.2]octyl, decalinyl, and adamantyl.

The term "aryl" refers to a monovalent monocyclic aromatic hydrocarbon radical and/or monovalent polycyclic aromatic hydrocarbon radical that contain at least one aromatic carbon ring. In certain embodiments, the aryl has from 6 to 20 ($C_{6-20}$), from 6 to 15 ($C_{6-15}$), or from 6 to 10 ($C_{6-10}$) ring carbon atoms. Examples of aryl groups include, but are not limited to, phenyl, naphthyl, fluorenyl, azulenyl, anthryl, phenanthryl, pyrenyl, biphenyl, and terphenyl. The aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In one embodiment, the aryl is monocyclic. In another embodiment, the aryl is polycyclic. In yet another embodiment, the aryl is bicyclic. In still another embodiment, the aryl is tricyclic. In certain embodiments, the aryl is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, the aralkyl is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms, each independently selected from O, S, and N, in the ring. The heteroaryl is bonded to the rest of a molecule through the aromatic ring. Each ring of a heteroaryl group can contain one or two O atoms, one or two S atoms, and/or one to four N atoms; provided that the total number of heteroatoms in each ring is four or less and each ring contains at least one carbon atom. In certain embodiments, the heteroaryl has from 5 to 20, from 5 to 15, or from 5 to 10 ring atoms. In one embodiment, the heteroaryl is monocyclic. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. In another embodiment, the heteroaryl is bicyclic. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. In yet another embodiment, the heteroaryl is tricyclic. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms, each independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. The heterocyclyl is bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclyls and heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein.

The term "halogen", "halide," or "halo" refers to fluorine, chlorine, bromine, and/or iodine.

The term "optionally substituted" is intended to mean that a group or substituent, such as an alkyl, alkenyl, alkynyl, cycloalkyl, aryl, aralkyl, heteroaryl, or heterocyclyl group, may be substituted with one or more, one, two, three, or four, substituents Q, each of which is independently selected from, e.g., (a) deuterium (-D), cyano (—CN), halo, and nitro (—$NO_2$); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(=N$R^a$)N$R^bR^c$, —OC(S)$R^a$, —OC(S)O$R^a$, —OC(S)N$R^bR^c$, —OS(O)$R^a$, —OS$(O)_2R^a$, —OS(O)N$R^bR^c$, —OS$(O)_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(=N$R^d$)N$R^bR^c$, —N$R^a$C(S)$R^d$, —N$R^a$C(S)O$R^d$, —N$R^a$C(S)N$R^bR^c$, —N$R^a$S(O)$R^d$, —N$R^a$S$(O)_2R^d$, —N$R^a$S(O)N$R^bR^c$, —N$R^a$S$(O)_2$N$R^bR^c$, —S$R^a$, —S(O)$R^a$, —S$(O)_2R^a$, —S(O)N$R^bR^c$, and —S$(O)_2$N$R^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(O)S$R^e$, —C(N$R^e$)N$R^fR^g$, —C(S)$R^e$, —C(S)O$R^e$, —C(S)N$R^fR^g$, —O$R^e$, —OC(O)$R^e$, —OC(O)O$R^e$, —OC(O)N$R^fR^g$, —OC(O)S$R^e$, —OC(=N$R^e$)N$R^fR^g$, —OC(S)$R^e$, —OC(S)O$R^e$, —OC(S)N$R^fR^g$, —OS(O)$R^e$, —OS$(O)_2R^e$, —OS(O)N$R^fR^g$, —OS$(O)_2$N$R^fR^g$, —N$R^fR^g$, —N$R^e$C(O)$R^h$, —N$R^e$C(O)O$R^f$, —N$R^e$C(O)N$R^fR^g$, —N$R^e$C(O)S$R^f$, —N$R^e$C(=N$R^h$)N$R^fR^g$, —N$R^e$C(S)$R^h$, —N$R^e$C(S)O$R^f$, —NR C(S)N$R^fR^g$, —N$R^e$S(O)$R^h$, —N$R^e$S$(O)_2R^h$, —N$R^e$S(O)N$R^fR^g$, —N$R^a$S$(O)_2$N$R^fR^g$, —S$R^e$, —S(O)$R^e$, —S$(O)_2R^e$, —S(O)N$R^fR^g$, and —S$(O)_2$N$R^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In certain embodiments, "optically active" and "enantiomerically active" refer to a collection of molecules, which has an enantiomeric excess of no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question. In certain embodiments, an optically active compound comprises about 98% or more of one enantiomer and about 2% or less of the other enantiomer based on the total weight of the enantiomeric mixture in question. In certain embodiments, an optically active compound comprises about 99% or more of one enantiomer and about 1% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen ($^{1}H$), deuterium ($^{2}H$), tritium ($^{3}H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$) iodine-127 ($^{127}I$), iodine-129 ($^{129}I$), and iodine-131 ($^{131}I$). In certain embodiments, an isotopically enriched compound is in a stable form, that is, non-radioactive. In certain embodiments, an isotopically enriched compound contains unnatural proportions of one or more isotopes, including, but not limited to, hydrogen ($^{1}H$), deuterium ($^{2}H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In certain embodiments, an isotopically enriched compound is in an unstable form, that is, radioactive. In certain embodiments, an isotopically enriched compound contains unnatural proportions of one or more isotopes, including, but not limited to, tritium ($^{3}H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$), and iodine-131 ($^{131}I$). It will be understood that, in a compound as provided herein, any hydrogen can be $^{2}H$, as example, or any carbon can be $^{13}C$, as example, or any nitrogen can be $^{15}N$, as example, or any oxygen can be $^{18}O$, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^{1}H$ for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium ($^{1}H$), deuterium ($^{2}H$ or D), and tritium ($^{3}H$), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}C$) and carbon-13 ($^{13}C$) in their natural abundances. Carbon-12 is the most common carbon isotope having a natural abundance of more than 98.89%. Carbon-13 is a less prevalent carbon isotope having a natural abundance of about 1.11%.

The term "carbon-13 enrichment" or "$^{13}C$ enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%).

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 95%, at least about 96%, at least about 97%, at least about 98%, at least about 99%, or at least about 99.5% by weight of the molecules are a single compound, including a single enantiomer, a racemic mixture, or a mixture of enantiomers, as determined by standard analytical methods. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which are present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "a diastereomer, a mixture of two or more diastereomers, a tautomer, a mixture of two or more tautomers, or an isotopic variant thereof; or a pharmaceutically acceptable salt, solvate, hydrate, or prodrug thereof" has the same meaning as the phrase "(i) a diastereomer, a mixture of two or more diastereomers, a tautomer, a mixture of two or more tautomers, or an isotopic variant of the compound referenced therein; or (ii) a pharmaceutically acceptable salt, solvate, hydrate, or prodrug of the compound referenced therein, or (iii) a pharmaceutically acceptable salt, solvate, hydrate, or prodrug of a diastereomer, a mixture of two or more diastereomers, a tautomer, a mixture of two or more tautomers, or an isotopic variant of the compound referenced therein."

MDM2 Inhibitors

In one embodiment, the MDM2 inhibitor provided herein is a compound of Formula (I):

(I)

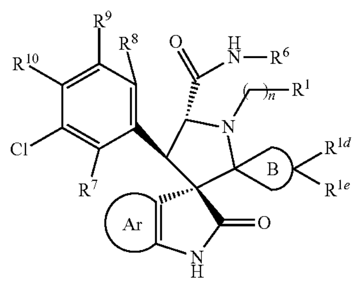

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

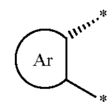

is

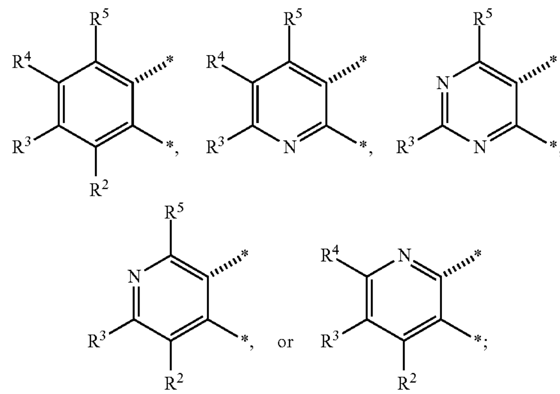

ring B is $C_{3-10}$ cycloalkyl or heterocyclyl;

$R^1$ is hydrogen, $C_{1-6}$ alkyl, $C_{3-10}$ cycloalkyl, heterocyclyl, $—NR^{1b}R^{1c}$, or $—OR^{1a}$; and n is an integer of 0, 1, or 2;

$R^2$, $R^3$, $R^4$, $R^5$, $R^7$, $R^8$, $R^9$, and $R^{10}$ are each independently hydrogen, fluoro, chloro, methyl, or trifluoromethyl;

$R^6$ is

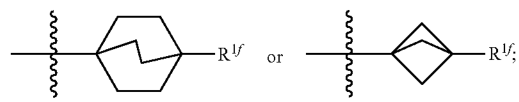

wherein each $R^{1f}$ is independently $—C(═O)OR^{1a}$, $—C(═O)NR^{1b}R^{1c}$, or $—C(═O)NHSO_2CH_3$;

$R^{1d}$ and $R^{1e}$ are each independently hydrogen, halo, $C_{1-6}$ alkyl, or $—OR^{1a}$; or $R^{1d}$ and $R^{1e}$ together with the carbon to which they are attached form $C_{3-10}$ cycloalkyl or heterocyclyl; and each $R^{1a}$, $R^{1b}$, and $R^{1c}$ is independently hydrogen or $C_{1-6}$ alkyl;

wherein each alkyl, cycloalkyl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) $—C(O)R^a$, $—C(O)OR^a$, $—C(O)NR^bR^c$, $—C(O)SR^a$, $—C(NR^a)NR^bR^c$, $—C(S)R^a$, $—C(S)OR^a$, $—C(S)NR^bR^c$, $—OR^a$, $—OC(O)R^a$, $—OC(O)OR^a$, $—OC(O)NR^bR^c$, $—OC(O)SR^a$, $—OC(═NR^a)NR^bR^c$, $—OC(S)R^a$, $—OC(S)OR^a$, $—OC(S)NR^bR^c$, $—OS(O)R^a$, $—OS(O)_2R^a$, $—OS(O)NR^bR^c$, $—OS(O)_2NR^bR^c$, $—NR^bR^c$, $—NR^aC(O)R^d$, $—NR^aC(O)OR^d$, $—NR^aC(O)NR^bR^c$, $—NR^aC(O)SR^d$, $—NR^aC(═NR^d)NR^bR^c$, $—NR^aC(S)R^d$, $—NR^aC(S)OR^d$, $—NR^aC(S)NR^bR^c$, $—NR^aS(O)R^d$, $—NR^aS(O)_2R^d$, $—NR^aS(O)NR^bR^c$, $—NR^aS(O)_2$ $NR^bR^c$, $—SR^a$, $—S(O)R^a$, $—S(O)_2R^a$, $—S(O)NR^bR^c$, and $—S(O)_2NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) $—C(O)R^e$, $—C(O)OR^e$, $—C(O)NR^fR^g$, $—C(O)SR^e$, $—C(NR^e)NR^fR^g$, $—C(S)R^e$, $—C(S)OR^e$, $—C(S)NR^fR^g$, $—OR^e$, $—OC(O)R^e$, $—OC(O)OR^e$, $—OC(O)NR^fR^g$, $—OC(O)SR^e$, $—OC(=NR^e)NR^fR^g$, $—OC(S)R^e$, $—OC(S)OR^e$, $—OC(S)NR^fR^g$, $—OS(O)R^e$, $—OS(O)_2R^e$, $—OS(O)NR^fR^g$, $—OS(O)_2NR^fR^g$, $—NR^fR^g$, $—NR^eC(O)R^h$, $—NR^eC(O)OR^f$, $—NR\ C(O)NR^fR^g$, $—NR^eC(O)SR^f$, $—NR^eC(=NR^h)NR^fR^g$, $—NR^eC(S)R^h$, $—NR^eC(S)OR^f$, $—NR\ C(S)NR^fR^g$, $—NR^eS(O)R^h$, $—NR^eS(O)_2R^h$, $—NR^eS(O)NR^fR^g$, $—NR^aS(O)_2NR^fR^g$, $—SR^e$, $—S(O)R^e$, $—S(O)_2R^e$, $—S(O)NR^fR^g$, and $—S(O)_2NR^fR^g$; wherein each $R^e$, $R^f$, $R^9$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In one embodiment, in Formula (I),

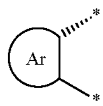

is

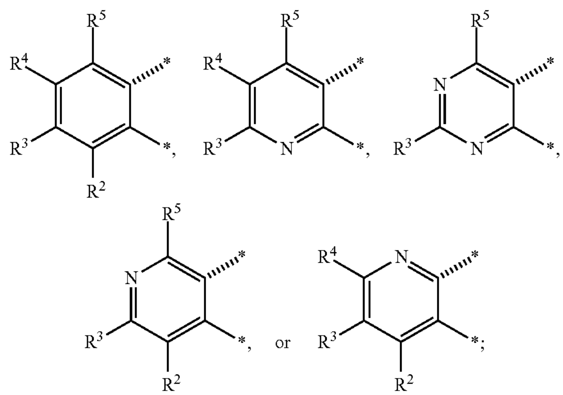

ring B is $C_{3-10}$ cycloalkyl or heterocyclyl;

$R^1$ is hydrogen, $C_{1-6}$ alkyl, $C_{3-10}$ cycloalkyl, heterocyclyl, $—NR^{1b}R^{1c}$, or $—OR^{1a}$; and n is an integer of 0, 1, or 2;

$R^2$, $R^4$, $R^5$, $R^8$, $R^9$, and $R^{10}$ are each independently hydrogen, fluoro, chloro, methyl, or trifluoromethyl;

$R^3$ is chloro;

$R^6$ is

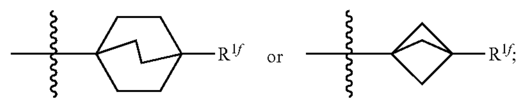

wherein each $R^{1f}$ is independently $—C(=O)OR^{1a}$, $—C(=O)NR^{1b}R^{1c}$, or $—C(=O)NHSO_2CH_3$;

$R^7$ is fluoro;

$R^{1d}$ and $R^{1e}$ are each independently hydrogen, halo, $C_{1-6}$ alkyl, or $—OR^{1a}$; or $R^{1d}$ and $R^{1e}$ together with the carbon to which they are attached form $C_{3-10}$ cycloalkyl or heterocyclyl; and each $R^{1a}$, $R^{1b}$, and $R^{1c}$ is independently hydrogen or $C_{1-6}$ alkyl;

wherein each alkyl, cycloalkyl, and heterocyclyl is optionally substituted with one or more, in one embodiment, one, two, three, or four, substituents Q.

In another embodiment, in Formula (I),

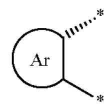

is

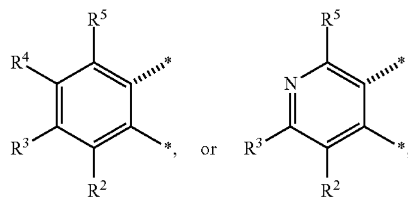

ring B is $C_{3-10}$ cycloalkyl;

$R^1$ is hydrogen or $C_{1-6}$ alkyl; and n is an integer of 0, 1, or 2;

$R^2$, $R^4$, $R^5$, $R^8$, $R^9$, and $R^{10}$ are each independently hydrogen, fluoro, chloro, methyl, or trifluoromethyl;

$R^3$ is chloro;

$R^6$ is

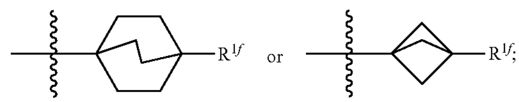

wherein each $R^{1f}$ is independently $—C(=O)OR^{1a}$, $—C(=O)NR^{1b}R^{1c}$, or $—C(=O)NHSO_2CH_3$;

$R^7$ is fluoro;

$R^{1d}$ and $R^{1e}$ are each independently hydrogen, halo, $C_{1-6}$ alkyl, or $—OR^{1a}$; and each $R^{1a}$, $R^{1b}$, and $R^{1c}$ is independently hydrogen or $C_{1-6}$ alkyl;

wherein each alkyl is independently substituted with one or more, in one embodiment, one, two, three, or four, substituents Q.

In yet another embodiment, in Formula (I),

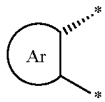

is

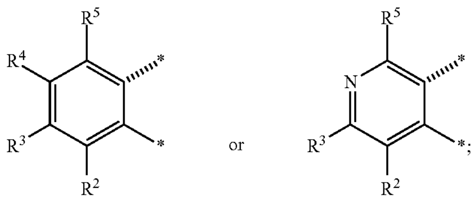

ring B is cyclohexyl or cyclobutyl;

$R^1$ is hydrogen, methyl, or ethyl; and n is an integer of 0;

$R^2$, $R^4$, $R^5$, $R^8$, $R^9$, and $R^{10}$ are each hydrogen;

$R^3$ is chloro;

$R^6$ is

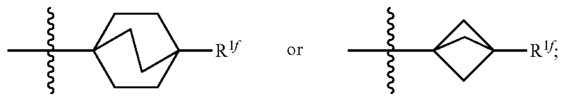

wherein each $R^{1f}$ is independently —C(═O)OH, —C(═O)$NH_2$, or —C(═O)$NHSO_2CH_3$;

$R^7$ is fluoro; and $R^{1d}$ and $R^{1e}$ are each independently hydrogen, fluoro, methyl, or hydroxy.

In still another embodiment, in Formula (I),

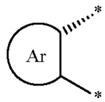

is

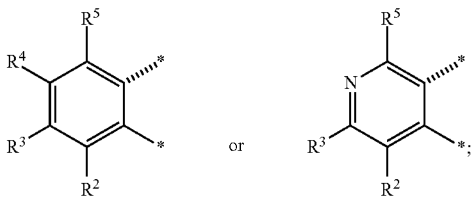

ring B together with $R^{1d}$ and $R^{1e}$ is 3,3-dimethylcyclobutyl, cyclohexyl, 4,4-difluorocyclohexyl, or 4-hydroxy-4-methyl-cyclohexyl;

$R^1$ is hydrogen, methyl, or ethyl; and n is an integer of 0;

$R^2$, $R^4$, $R^5$, $R^8$, $R^9$, and $R^{10}$ are each hydrogen;

$R^3$ is chloro;

$R^6$ is

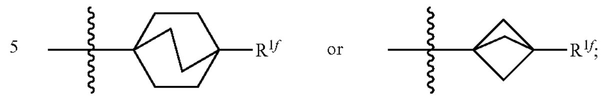

wherein each $R^{1f}$ is independently —C(═O)OH, —C(═O)$NH_2$, or —C(═O)$NHSO_2CH_3$; and $R^7$ is fluoro.

In another embodiment, the MDM2 inhibitor provided herein is a compound of Formula (II):

(II)

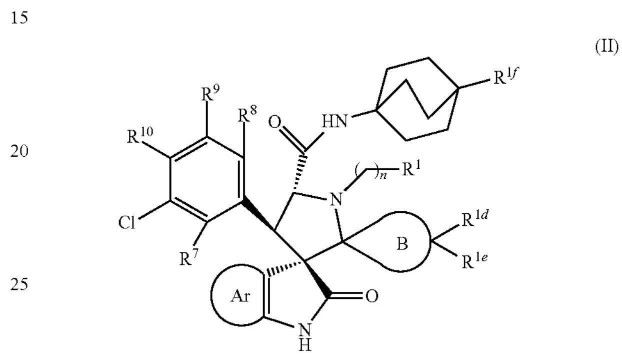

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^7$, $R^8$, $R^9$, $R^{10}$, $R^{1d}$, $R^{1e}$, $R^{1f}$, ring Ar, ring B, and n are each as defined herein.

In yet another embodiment, the MDM2 inhibitor provided herein is a compound of Formula (III):

(III)

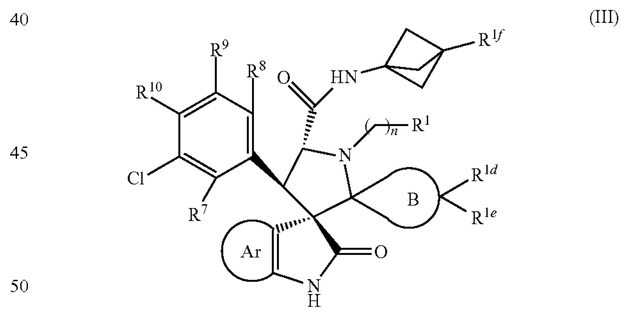

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^7$, $R^8$, $R^9$, $R^{10}$, $R^{1d}$, $R^{1e}$, $R^{1f}$, ring Ar, ring B, and n are each as defined herein.

In one embodiment, in Formula (II) or (III),

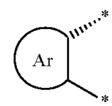

is

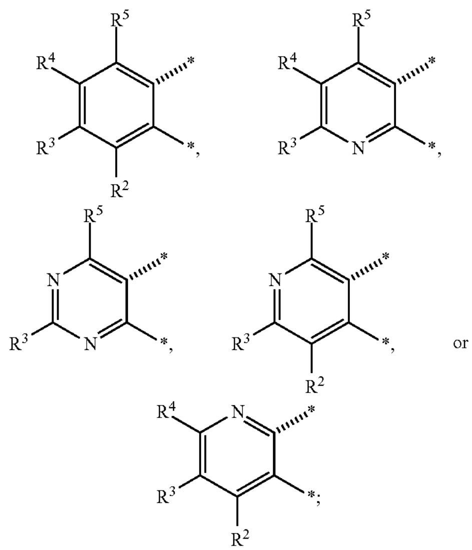

ring B is $C_{3-10}$ cycloalkyl or heterocyclyl;

$R^1$ is hydrogen, $C_{1-6}$ alkyl, $C_{3-10}$ cycloalkyl, heterocyclyl, $—NR^{1b}R^{1c}$, or $—OR^{1a}$; and n is an integer of 0, 1, or 2;

$R^2$, $R^4$, $R^5$, $R^8$, $R^9$, and $R^{10}$ are each independently hydrogen, fluoro, chloro, methyl, or trifluoromethyl;

$R^3$ is chloro;

$R^7$ is fluoro;

$R^{1d}$ and $R^{1e}$ are each independently hydrogen, halo, $C_{1-6}$ alkyl, or $—OR^{1a}$; or $R^{1d}$ and $R^{1e}$ together with the carbon to which they are attached form $C_{3-10}$ cycloalkyl or heterocyclyl; and $R^{1f}$ is $—C(═O)OR^{1a}$, $—C(═O)NR^{1b}R^{1c}$, or $—C(═O)NHSO_2CH_3$; and each $R^{1a}$, $R^{1b}$, and $R^{1c}$ is independently hydrogen or $C_{1-6}$ alkyl;

wherein each alkyl, cycloalkyl, and heterocyclyl is optionally substituted with one or more, in one embodiment, one, two, three, or four, substituents Q.

In another embodiment, in Formula (II) or (III),

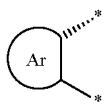

is

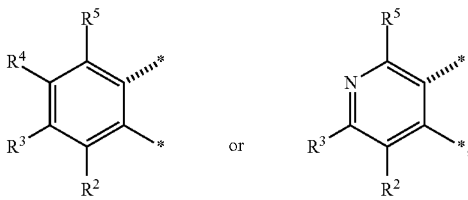

ring B is $C_{3-10}$ cycloalkyl;

$R^1$ is hydrogen or $C_{1-6}$ alkyl; and n is an integer of 0, 1, or 2;

$R^2$, $R^4$, $R^5$, $R^8$, $R^9$, and $R^{10}$ are each independently hydrogen, fluoro, chloro, methyl, or trifluoromethyl;

$R^3$ is chloro;

$R^7$ is fluoro;

$R^{1d}$ and $R^{1e}$ are each independently hydrogen, halo, $C_{1-6}$ alkyl, or $—OR^{1a}$;

$R^{1f}$ is $—C(═O)OR^{1a}$, $—C(═O)NR^{1b}R^{1c}$, or $—C(═O)NHSO_2CH_3$; and each $R^{1a}$, $R^{1b}$, and $R^{1c}$ is independently hydrogen or $C_{1-6}$ alkyl;

wherein each alkyl is independently substituted with one or more, in one embodiment, one, two, three, or four, substituents Q.

In yet another embodiment, in Formula (II) or (III),

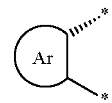

is

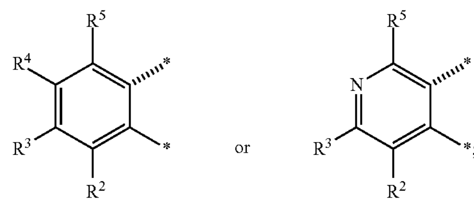

ring B is cyclohexyl or cyclobutyl;

$R^1$ is hydrogen, methyl, or ethyl; and n is an integer of 0;

$R^2$, $R^4$, $R^5$, $R^8$, $R^9$, and $R^{10}$ are each hydrogen;

$R^3$ is chloro;

$R^7$ is fluoro;

$R^{1d}$ and $R^{1e}$ are each independently hydrogen, fluoro, methyl, or hydroxy; and $R^{1f}$ is $—C(═O)OH$, $—C(═O)NH_2$, or $—C(═O)NHSO_2CH_3$.

In still another embodiment, in Formula (II) or (III),

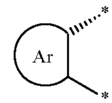

is

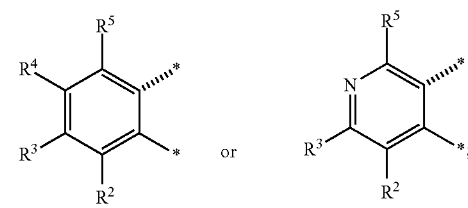

ring B together with $R^{1d}$ and $R^{1e}$ is 3,3-dimethylcyclobutyl, cyclohexyl, 4,4-difluorocyclohexyl, or 4-hydroxy-4-methyl-cyclohexyl;

$R^1$ is hydrogen, methyl, or ethyl; and n is an integer of 0;

$R^2$, $R^4$, $R^5$, $R^8$, $R^9$, and $R^{10}$ are each hydrogen;

$R^3$ is chloro;

$R^7$ is fluoro; and $R^{1f}$ is —C(=O)OH, —C(=O)$NH_2$, or —C(=O)$NHSO_2CH_3$.

In yet another embodiment, the MDM2 inhibitor provided herein is a compound of Formula (IV):

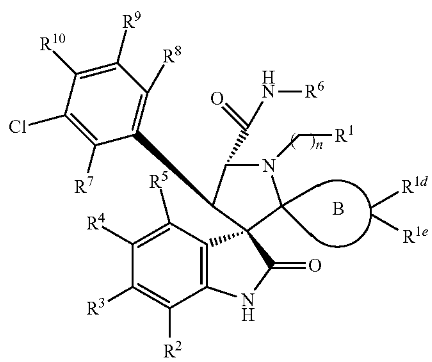

(IV)

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, $R^7$, $R^8$, $R^9$, $R^{10}$, $R^{1d}$, $R^{1e}$, ring B, and n are each as defined herein.

In one embodiment, in Formula (IV), ring B is $C_{3-10}$ cycloalkyl or heterocyclyl;

$R^1$ is hydrogen, $C_{1-6}$ alkyl, $C_{3-10}$ cycloalkyl, heterocyclyl, —$NR^{1b}R^{1c}$, or —$OR^{1a}$; and n is an integer of 0, 1, or 2;

$R^2$, $R^4$, $R^5$, $R^8$, $R^9$, and $R^{10}$ are each independently hydrogen, fluoro, chloro, methyl, or trifluoromethyl;

$R^3$ is chloro;

$R^6$ is

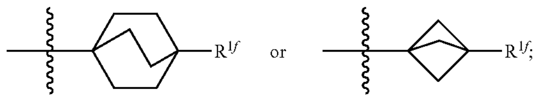

wherein each $R^{1f}$ is independently —C(=O)$OR^{1a}$, —C(=O)$NR^{1b}R^{1c}$, or —C(=O)$NHSO_2CH_3$;

$R^7$ is fluoro;

$R^{1d}$ and $R^{1e}$ are each independently hydrogen, halo, $C_{1-6}$ alkyl, or —$OR^{1a}$; or $R^{1d}$ and $R^{1e}$ together with the carbon to which they are attached form $C_{3-10}$ cycloalkyl or heterocyclyl; and each $R^{1a}$, $R^{1b}$, and $R^{1c}$ is independently hydrogen or $C_{1-6}$ alkyl;

wherein each alkyl, cycloalkyl, and heterocyclyl is optionally substituted with one or more, in one embodiment, one, two, three, or four, substituents Q.

In another embodiment, in Formula (IV), ring B is $C_{3-10}$ cycloalkyl;

$R^1$ is hydrogen or $C_{1-6}$ alkyl; and n is an integer of 0, 1, or 2;

$R^2$, $R^4$, $R^5$, $R^8$, $R^9$, and $R^{10}$ are each independently hydrogen, fluoro, chloro, methyl, or trifluoromethyl;

$R^3$ is chloro;

$R^6$ is

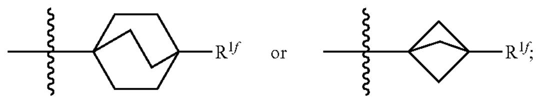

wherein each $R^{1f}$ is independently —C(=O)$OR^{1a}$, —C(=O)$NR^{1b}R^{1c}$, or —C(=O)$NHSO_2CH_3$;

$R^7$ is fluoro;

$R^{1d}$ and $R^{1e}$ are each independently hydrogen, halo, $C_{1-6}$ alkyl, or —$OR^{1a}$; and each $R^{1a}$, $R^{1b}$, and $R^{1c}$ is independently hydrogen or $C_{1-6}$ alkyl;

wherein each alkyl is independently substituted with one or more, in one embodiment, one, two, three, or four, substituents Q.

In yet another embodiment, in Formula (IV), ring B is cyclohexyl or cyclobutyl;

$R^1$ is hydrogen, methyl, or ethyl; and n is an integer of 0;

$R^2$, $R^4$, $R^5$, $R^8$, $R^9$, and $R^{10}$ are each hydrogen;

$R^3$ is chloro;

$R^6$ is

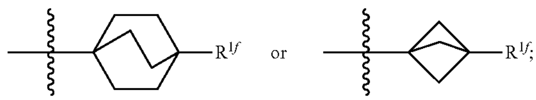

wherein each $R^{1f}$ is independently —C(=O)OH, —C(=O)$NH_2$, or —C(=O)$NHSO_2CH_3$;

$R^7$ is fluoro; and $R^{1d}$ and $R^{1e}$ are each independently hydrogen, fluoro, methyl, or hydroxy.

In still another embodiment, in Formula (IV), ring B together with $R^{1d}$ and $R^{1e}$ is 3,3-dimethylcyclobutyl, cyclohexyl, 4,4-difluorocyclohexyl, or 4-hydroxy-4-methyl-cyclohexyl;

$R^1$ is hydrogen, methyl, or ethyl; and n is an integer of 0;

$R^2$, $R^4$, $R^5$, $R^8$, $R^9$, and $R^{10}$ are each hydrogen;

$R^3$ is chloro;

$R^6$ is

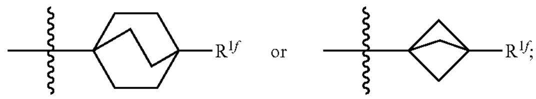

wherein each $R^{1f}$ is independently —C(=O)OH, —C(=O)$NH_2$, or —C(=O)$NHSO_2CH_3$; and $R^7$ is fluoro.

In yet another embodiment, the MDM2 inhibitor provided herein is a compound of Formula (V):

(V)

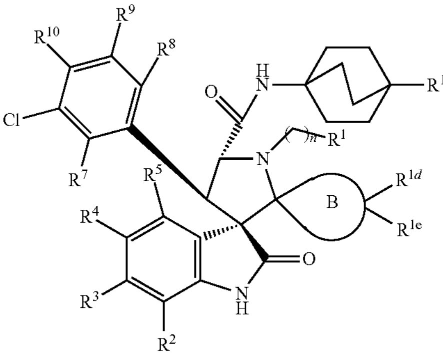

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^7$, $R^8$, $R^9$, $R^{10}$, $R^{1d}$, $R^{1e}$, $R^{1f}$, ring B, and n are each as defined herein.

In yet another embodiment, the MDM2 inhibitor provided herein is a compound of Formula (VI):

(VI)

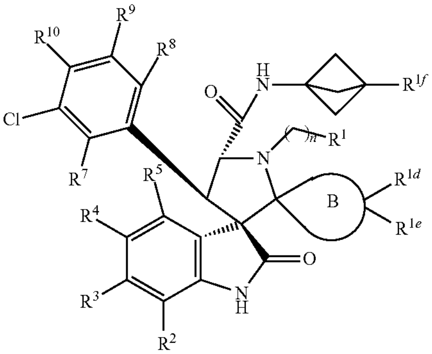

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^7$, $R^8$, $R^9$, $R^{10}$, $R^{1d}$, $R^{1e}$, $R^{1f}$, ring B, and n are each as defined herein.

In one embodiment, in Formula (V) or (VI), ring B is $C_{3-10}$ cycloalkyl or heterocyclyl;

$R^1$ is hydrogen, $C_{1-6}$ alkyl, $C_{3-10}$ cycloalkyl, heterocyclyl, —$NR^{1b}R^{1c}$, or —$OR^{1a}$; and n is an integer of 0, 1, or 2;

$R^2$, $R^4$, $R^5$, $R^8$, $R^9$, and $R^{10}$ are each independently hydrogen, fluoro, chloro, methyl, or trifluoromethyl;

$R^3$ is chloro;

$R^7$ is fluoro;

$R^{1d}$ and $R^{1e}$ are each independently hydrogen, halo, $C_{1-6}$ alkyl, or —$OR^{1a}$; or $R^{1d}$ and $R^{1e}$ together with the carbon to which they are attached form $C_{3-10}$ cycloalkyl or heterocyclyl;

$R^{1f}$ is —C(═O)$OR^{1a}$, —C(═O)$NR^{1b}R^{1c}$, or —C(═O)$NHSO_2CH_3$; and each $R^{1a}$, $R^{1b}$, and $R^{1c}$ is independently hydrogen or $C_{1-6}$ alkyl;

wherein each alkyl, cycloalkyl, and heterocyclyl is optionally substituted with one or more, in one embodiment, one, two, three, or four, substituents Q.

In another embodiment, in Formula (V) or (VI), ring B is $C_{3-10}$ cycloalkyl;

$R^1$ is hydrogen or $C_{1-6}$ alkyl; and n is an integer of 0, 1, or 2;

$R^2$, $R^4$, $R^5$, $R^8$, $R^9$, and $R^{10}$ are each independently hydrogen, fluoro, chloro, methyl, or trifluoromethyl;

$R^3$ is chloro;

$R^7$ is fluoro;

$R^{1d}$ and $R^{1e}$ are each independently hydrogen, halo, $C_{1-6}$ alkyl, or —$OR^{1a}$;

$R^{1f}$ is —C(═O)$OR^{1a}$, —C(═O)$NR^{1a}R^{1b}$, or —C(═O)$NHSO_2CH_3$; and each $R^{1a}$, $R^{1b}$, and $R^{1c}$ is independently hydrogen or $C_{1-6}$ alkyl;

wherein each alkyl is independently substituted with one or more, in one embodiment, one, two, three, or four, substituents Q.

In yet another embodiment, in Formula (V) or (VI), ring B is cyclohexyl or cyclobutyl;

$R^1$ is hydrogen, methyl, or ethyl; and n is an integer of 0;

$R^2$, $R^4$, $R^5$, $R^8$, $R^9$, and $R^{10}$ are each hydrogen;

$R^3$ is chloro;

$R^7$ is fluoro;

$R^{1d}$ and $R^{1e}$ are each independently hydrogen, fluoro, methyl, or hydroxy; and $R^{1f}$ is —C(═O)OH, —C(═O)$NH_2$, or —C(═O)$NHSO_2CH_3$.

In still another embodiment, in Formula (V) or (VI), ring B together with $R^{1d}$ and $R^{1e}$ is 3,3-dimethylcyclobutyl, cyclohexyl, 4,4-difluorocyclohexyl, or 4-hydroxy-4-methyl-cyclohexyl;

$R^1$ is hydrogen, methyl, or ethyl; and n is an integer of 0;

$R^2$, $R^4$, $R^5$, $R^8$, $R^9$, and $R^{10}$ are each hydrogen;

$R^3$ is chloro;

$R^7$ is fluoro; and $R^{1f}$ is —C(═O)OH, —C(═O)$NH_2$, or —C(═O)$NHSO_2CH_3$.

In yet another embodiment, the MDM2 inhibitor provided herein is a compound of Formula (VII):

(VII)

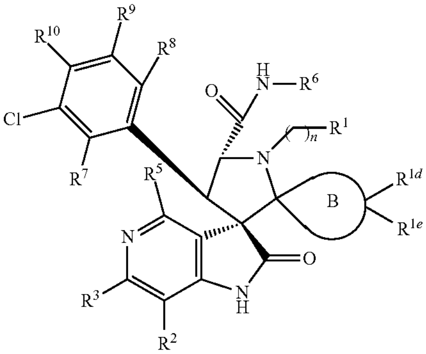

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, $R^7$, $R^8$, $R^9$, $R^{10}$, $R^{1d}$, $R^{1e}$, ring B, and n are each as defined herein.

In one embodiment, in Formula (VII), ring B is $C_{3-10}$ cycloalkyl or heterocyclyl;

$R^1$ is hydrogen, $C_{1-6}$ alkyl, $C_{3-10}$ cycloalkyl, heterocyclyl, —$NR^{1b}R^{1c}$, or —$OR^{1a}$; and n is an integer of 0, 1, or 2;

$R^2$, $R^5$, $R^8$, $R^9$, and $R^{10}$ are each independently hydrogen, fluoro, chloro, methyl, or trifluoromethyl;

$R^3$ is chloro;

$R^6$ is

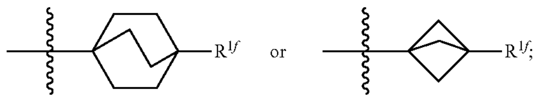

wherein each $R^{1f}$ is independently —C(═O)OR$^{1a}$, —C(═O)NR$^{1b}$R$^{1c}$, or —C(═O)NHSO$_2$CH$_3$;

$R^7$ is fluoro;

$R^{1d}$ and $R^{1e}$ are each independently hydrogen, halo, $C_{1-6}$ alkyl, or —OR$^{1a}$; or $R^{1d}$ and $R^{1e}$ together with the carbon to which they are attached form $C_{3-10}$ cycloalkyl or heterocyclyl; and each $R^{1a}$, $R^{1b}$, and $R^{1c}$ is independently hydrogen or $C_{1-6}$ alkyl;

wherein each alkyl, cycloalkyl, and heterocyclyl is optionally substituted with one or more, in one embodiment, one, two, three, or four, substituents Q.

In another embodiment, in Formula (VII), ring B is $C_{3-10}$ cycloalkyl;

$R^1$ is hydrogen or $C_{1-6}$ alkyl; and n is an integer of 0, 1, or 2;

$R^2$, $R^5$, $R^8$, $R^9$, and $R^{10}$ are each independently hydrogen, fluoro, chloro, methyl, or trifluoromethyl;

$R^3$ is chloro;

$R^6$ is

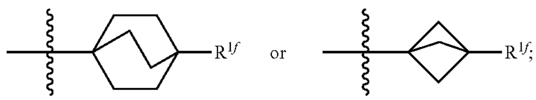

wherein each $R^{1f}$ is independently —C(═O)OR$^{1a}$, —C(═O)NR$^{1b}$R$^{1c}$, or —C(═O)NHSO$_2$CH$_3$;

$R^7$ is fluoro;

$R^{1d}$ and $R^{1e}$ are each independently hydrogen, halo, $C_{1-6}$ alkyl, or —OR$^{1a}$; and each $R^{1a}$, $R^{1b}$, and $R^{1c}$ is independently hydrogen or $C_{1-6}$ alkyl;

wherein each alkyl is independently substituted with one or more, in one embodiment, one, two, three, or four, substituents Q.

In yet another embodiment, in Formula (VII), ring B is cyclohexyl or cyclobutyl;

$R^1$ is hydrogen, methyl, or ethyl; and n is an integer of 0;

$R^2$, $R^5$, $R^8$, $R^9$, and $R^{10}$ are each hydrogen;

$R^3$ is chloro;

$R^6$ is

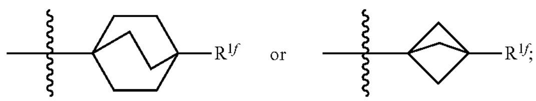

wherein each $R^{1f}$ is independently —C(═O)OH, —C(═O)NH$_2$, or —C(═O)NHSO$_2$CH$_3$;

$R^7$ is fluoro; and $R^{1d}$ and $R^{1e}$ are each independently hydrogen, fluoro, methyl, or hydroxy.

In still another embodiment, in Formula (VII), ring B together with $R^{1d}$ and $R^{1e}$ is 3,3-dimethylcyclobutyl, cyclohexyl, 4,4-difluorocyclohexyl, or 4-hydroxy-4-methyl-cyclohexyl;

$R^1$ is hydrogen, methyl, or ethyl; and n is an integer of 0;

$R^2$, $R^5$, $R^8$, $R^9$, and $R^{10}$ are each hydrogen;

$R^3$ is chloro;

$R^6$ is

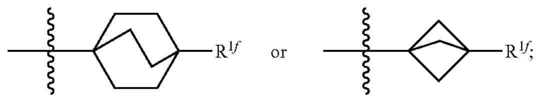

wherein each $R^{1f}$ is independently —C(═O)OH, —C(═O)NH$_2$, or —C(═O)NHSO$_2$CH$_3$; and $R^7$ is fluoro.

In yet another embodiment, the MDM2 inhibitor provided herein is a compound of Formula (VIII):

(VIII)

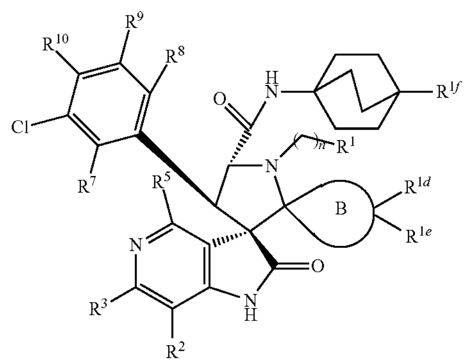

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^7$, $R^8$, $R^9$, $R^{10}$, $R^{1d}$, $R^{1e}$, $R^{1f}$, ring B, and n are each as defined herein.

In still another embodiment, the MDM2 inhibitor provided herein is a compound of Formula (IX):

(IX)

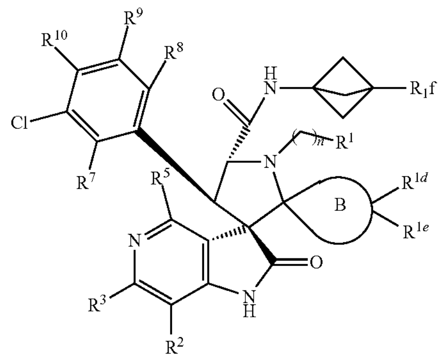

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^7$, $R^8$, $R^9$, $R^{10}$, $R^{1d}$, $R^{1e}$, $R^{1f}$, ring B, and n are each as defined herein.

In one embodiment, in Formula (VIII) or (IX), ring B is $C_{3-10}$ cycloalkyl or heterocyclyl;

$R^1$ is hydrogen, $C_{1-6}$ alkyl, $C_{3-10}$ cycloalkyl, heterocyclyl, —$NR^{1b}R^{1c}$, or —$OR^{1a}$; and n is an integer of 0, 1, or 2;

$R^2$, $R^5$, $R^8$, $R^9$, and $R^{10}$ are each independently hydrogen, fluoro, chloro, methyl, or trifluoromethyl;

$R^3$ is chloro;

$R^7$ is fluoro;

$R^{1d}$ and $R^{1e}$ are each independently hydrogen, halo, $C_{1-6}$ alkyl, or —$OR^{1a}$; or $R^{1d}$ and $R^{1e}$ together with the carbon to which they are attached form $C_{3-10}$ cycloalkyl or heterocyclyl;

$R^{1f}$ is —C(═O)$OR^{1a}$, —C(═O)$NR^{1b}R^{1c}$, or —C(═O)$NHSO_2CH_3$; and each $R^{1a}$, $R^{1b}$, and $R^{1c}$ is independently hydrogen or $C_{1-6}$ alkyl;

wherein each alkyl, cycloalkyl, and heterocyclyl is optionally substituted with one or more, in one embodiment, one, two, three, or four, substituents Q.

In another embodiment, in Formula (VIII) or (IX), ring B is $C_{3-10}$ cycloalkyl;

$R^1$ is hydrogen or $C_{1-6}$ alkyl; and n is an integer of 0, 1, or 2;

$R^2$, $R^5$, $R^8$, $R^9$, and $R^{10}$ are each independently hydrogen, fluoro, chloro, methyl, or trifluoromethyl;

$R^3$ is chloro;

$R^7$ is fluoro;

$R^{1d}$ and $R^{1e}$ are each independently hydrogen, halo, $C_{1-6}$ alkyl, or —$OR^{1a}$;

$R^{1f}$ is —C(═O)$OR^{1a}$, —C(═O)$NR^{1b}R^{1c}$, or —C(═O)$NHSO_2CH_3$; and each $R^{1a}$, $R^{1b}$, and $R^{1c}$ is independently hydrogen or $C_{1-6}$ alkyl;

wherein each alkyl is independently substituted with one or more, in one embodiment, one, two, three, or four, substituents Q.

In yet another embodiment, in Formula (VIII) or (IX), ring B is cyclohexyl or cyclobutyl;

$R^1$ is hydrogen, methyl, or ethyl; and n is an integer of 0;

$R^2$, $R^5$, $R^8$, $R^9$, and $R^{10}$ are each hydrogen;

$R^3$ is chloro;

$R^7$ is fluoro;

$R^{1d}$ and $R^{1e}$ are each independently hydrogen, fluoro, methyl, or hydroxy; and $R^{1f}$ is —C(═O)OH, —C(═O)$NH_2$, or —C(═O)$NHSO_2CH_3$.

In still another embodiment, in Formula (VIII) or (IX), ring B together with $R^{1d}$ and $R^{1e}$ is 3,3-dimethylcyclobutyl, cyclohexyl, 4,4-difluorocyclohexyl, or 4-hydroxy-4-methyl-cyclohexyl;

$R^1$ is hydrogen, methyl, or ethyl; and n is an integer of 0;

$R^2$, $R^5$, $R^8$, $R^9$, and $R^{10}$ are each hydrogen;

$R^3$ is chloro;

$R^7$ is fluoro; and $R^{1f}$ is —C(═O)OH, —C(═O)$NH_2$, or —C(═O)$NHSO_2CH_3$.

The groups, $R^1$, $R^2$, $R^3$, $R^4$, $R^5$, $R^6$, $R^7$, $R^8$, $R^9$, $R^{10}$, $R^{1a}$, $R^{1b}$, $R^{1c}$, $R^{1d}$, $R^{1e}$, $R^{1f}$, ring Ar, ring B, and n, in formulae described herein, including Formulae I to IX, are further defined in the embodiments described herein. All combinations of the embodiments provided herein for such groups are within the scope of this disclosure.

In certain embodiments, $R^1$ is hydrogen. In certain embodiments, $R^1$ is $C_{1-6}$ alkyl, optionally substituted with one or more substituents Q. In certain embodiments, $R^1$ is methyl or ethyl, each optionally substituted with one or more substituents Q. In certain embodiments, $R^1$ is $C_{3-10}$ cycloalkyl, optionally substituted with one or more substituents Q. In certain embodiments, R is heterocyclyl, optionally substituted with one or more substituents Q. In certain embodiments, $R^1$ is —$OR^{1a}$, wherein $R^{1a}$ is as defined herein. In certain embodiments, R is —$NR^{1b}R^{1c}$, wherein $R^{1b}$ and $R^{1c}$ are each as defined herein. In certain embodiments, $R^1$ is hydrogen, methyl, or ethyl.

In certain embodiments, $R^2$ is hydrogen. In certain embodiments, $R^2$ is fluoro. In certain embodiments, $R^2$ is chloro. In certain embodiments, $R^2$ is methyl. In certain embodiments, $R^2$ is trifluoromethyl.

In certain embodiments, $R^3$ is hydrogen. In certain embodiments, $R^3$ is fluoro. In certain embodiments, $R^3$ is chloro. In certain embodiments, $R^3$ is methyl. In certain embodiments, $R^3$ is trifluoromethyl.

In certain embodiments, $R^4$ is hydrogen. In certain embodiments, $R^4$ is fluoro. In certain embodiments, $R^4$ is chloro. In certain embodiments, $R^4$ is methyl. In certain embodiments, $R^4$ is trifluoromethyl.

In certain embodiments, $R^5$ is hydrogen. In certain embodiments, $R^5$ is fluoro. In certain embodiments, $R^5$ is chloro. In certain embodiments, $R^5$ is methyl. In certain embodiments, $R^5$ is trifluoromethyl.

In certain embodiments, $R^6$ is

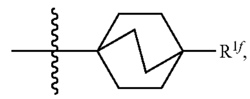

wherein $R^{1f}$ is as defined herein. In certain embodiments, $R^6$ is

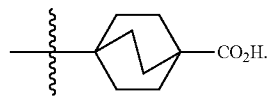

In certain embodiments, $R^6$ is

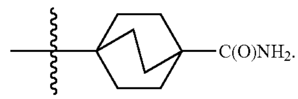

In certain embodiments, $R^6$ is

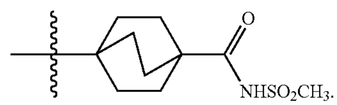

In certain embodiments, $R^6$ is

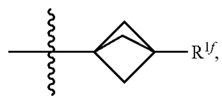

wherein $R^{1f}$ is as defined herein. In certain embodiments, $R^6$ is

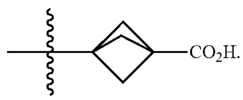 [SMILES: *C12CC(C(=O)O)(C1)C2]

In certain embodiments, $R^6$ is

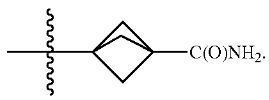

In certain embodiments, $R^6$ is

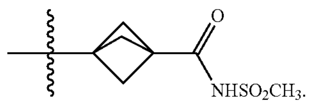

In certain embodiments, $R^7$ is hydrogen. In certain embodiments, $R^7$ is fluoro. In certain embodiments, $R^7$ is chloro. In certain embodiments, $R^7$ is methyl. In certain embodiments, $R^7$ is trifluoromethyl.

In certain embodiments, $R^8$ is hydrogen. In certain embodiments, $R^8$ is fluoro. In certain embodiments, $R^8$ is chloro. In certain embodiments, $R^8$ is methyl. In certain embodiments, $R^8$ is trifluoromethyl.

In certain embodiments, $R^9$ is hydrogen. In certain embodiments, $R^9$ is fluoro. In certain embodiments, $R^9$ is chloro. In certain embodiments, $R^9$ is methyl. In certain embodiments, $R^9$ is trifluoromethyl.

In certain embodiments, $R^{10}$ is hydrogen. In certain embodiments, $R^{10}$ is fluoro. In certain embodiments, $R^{10}$ is chloro. In certain embodiments, $R^{10}$ is methyl. In certain embodiments, $R^{10}$ is trifluoromethyl.

In certain embodiments, $R^{1a}$ is hydrogen. In certain embodiments, $R^{1a}$ is $C_{1-6}$ alkyl, optionally substituted with one or more substituents Q.

In certain embodiments, $R^{1b}$ is hydrogen. In certain embodiments, $R^{1b}$ is $C_{1-6}$ alkyl, optionally substituted with one or more substituents Q.

In certain embodiments, $R^{1c}$ is hydrogen. In certain embodiments, $R^{1c}$ is $C_{1-6}$ alkyl, optionally substituted with one or more substituents Q.

In certain embodiments, $R^{1d}$ is hydrogen. In certain embodiments, $R^{1d}$ is halo. In certain embodiments, $R^{1d}$ is fluoro. In certain embodiments, $R^{1d}$ is $C_{1-6}$ alkyl, optionally substituted with one or more substituents Q. In certain embodiments, $R^{1d}$ is methyl, optionally substituted with one or more substituents Q. In certain embodiments, $R^{1d}$ is —$OR^{1a}$, wherein $R^{1a}$ is as defined herein. In certain embodiments, $R^{1d}$ is —OH. In certain embodiments, $R^{1d}$ is hydrogen, fluoro, methyl, or hydroxy.

In certain embodiments, $R^{1e}$ is hydrogen. In certain embodiments, $R^{1e}$ is halo. In certain embodiments, $R^{1e}$ is fluoro. In certain embodiments, $R^{1e}$ is $C_{1-6}$ alkyl, optionally substituted with one or more substituents Q. In certain embodiments, $R^{1e}$ is methyl, optionally substituted with one or more substituents Q. In certain embodiments, $R^{1e}$ is —$OR^{1a}$, wherein $R^{1a}$ is as defined herein. In certain embodiments, $R^{1e}$ is —OH. In certain embodiments, $R^{1e}$ is hydrogen, fluoro, methyl, or hydroxy.

In certain embodiments, $R^{1d}$ and $R^{1e}$ together with the carbon to which they are attached form $C_{3-10}$ cycloalkyl, optionally substituted with one or more substituents Q. In certain embodiments, $R^{1d}$ and $R^{1e}$ together with the carbon to which they are attached form heterocyclyl, optionally substituted with one or more substituents Q.

In certain embodiments, $R^{1f}$ is —C(═O)$OR^{1a}$, wherein $R^{1a}$ is as defined herein. In certain embodiments, $R^{1f}$ is —C(═O)OH. In certain embodiments, $R^{1f}$ is —C(═O)$NR^{1b}R^{1c}$, wherein $R^{1b}$ and $R^{1c}$ are each as defined herein. In certain embodiments, $R^{1f}$ is —C(═O)$NH_2$. In certain embodiments, $R^{1f}$ is —C(═O)$NHSO_2CH_3$.

In certain embodiments, ring Ar is

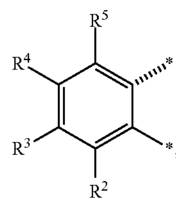

wherein $R^2$, $R^3$, $R^4$, and $R^5$ are each as defined herein. In certain embodiments, ring Ar is

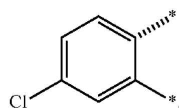

In certain embodiments, ring Ar is

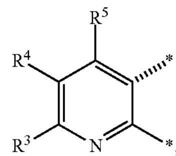

wherein $R^3$, $R^4$, and $R^5$ are each as defined herein. In certain embodiments, ring Ar is

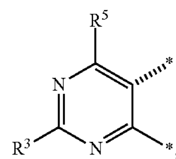

wherein $R^3$ and $R^5$ are each as defined herein. In certain embodiments, ring Ar is

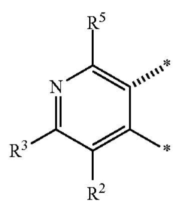

wherein $R^2$, $R^3$, and $R^5$ are each as defined herein. In certain embodiments, ring Ar is

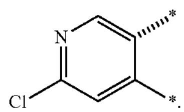

In certain embodiments, ring Ar is

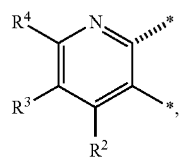

wherein $R^2$, $R^3$, and $R^4$ are each as defined herein.

In certain embodiments, ring B is $C_{3-10}$ cycloalkyl, optionally substituted with one or more substituents Q. In certain embodiments, ring B is cyclobutyl or cyclohexyl, each optionally substituted with one or more substituents Q. In certain embodiments, ring B is cyclobutyl or cyclohexyl, each optionally substituted with one or two $C_{1-6}$ alkyl. In certain embodiments, ring B is cyclobutyl or cyclohexyl, each optionally substituted with one or two methyl. In certain embodiments, ring B is heterocyclyl, optionally substituted with one or more substituents Q.

In certain embodiments, n is an integer of 0. In certain embodiments, n is an integer of 1. In certain embodiments, n is an integer of 2.

In one embodiment, the MDM2 inhibitor provided herein is:

A1

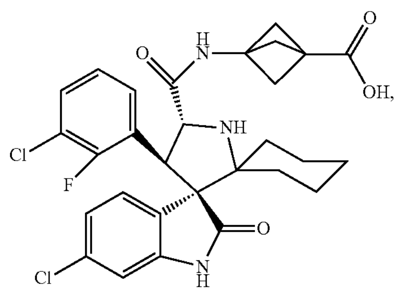

-continued

A2

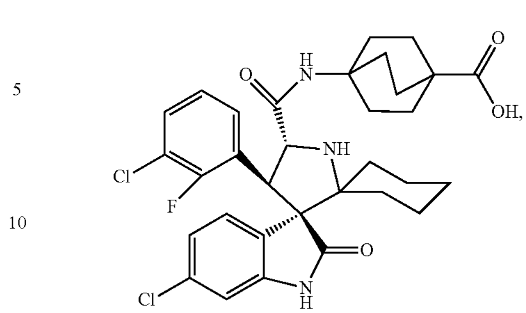

A3

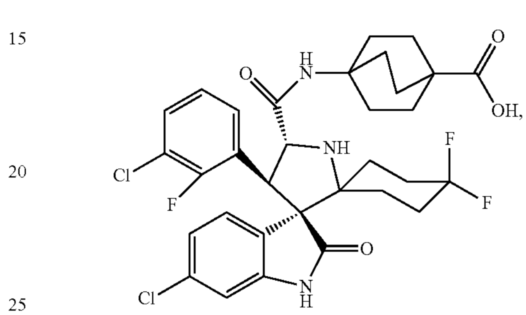

A4

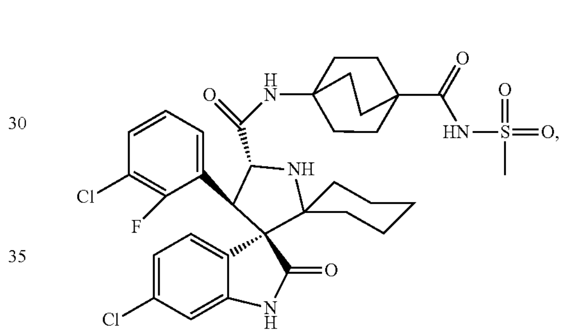

A5

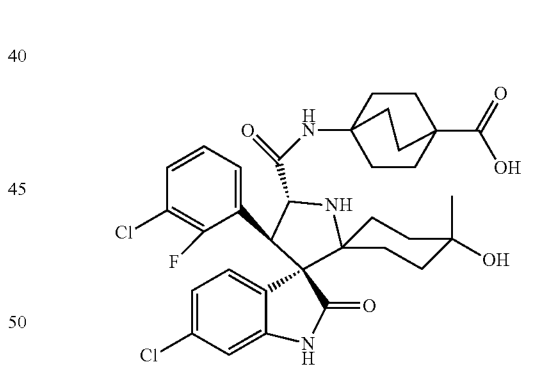

A6

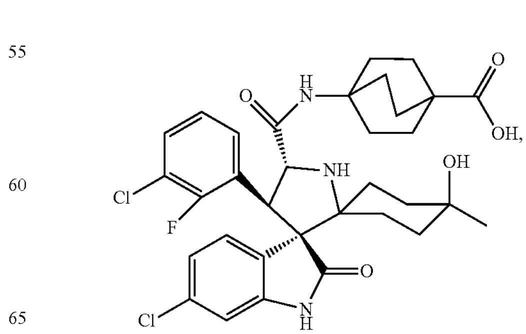

-continued

A7

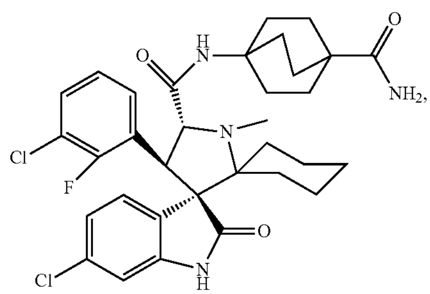

A8

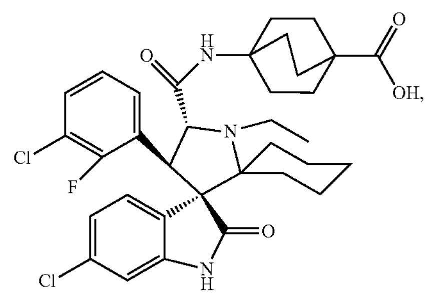

A9

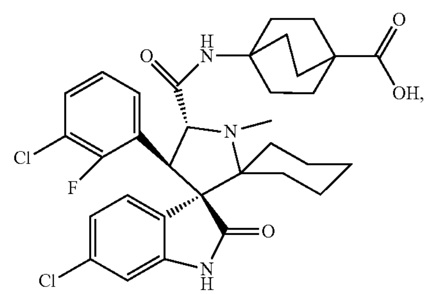

A10

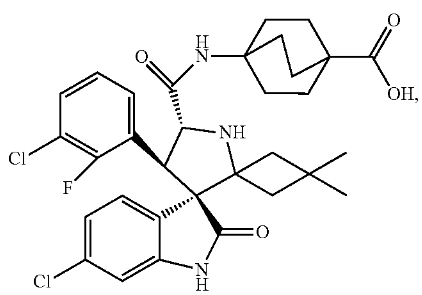

A11

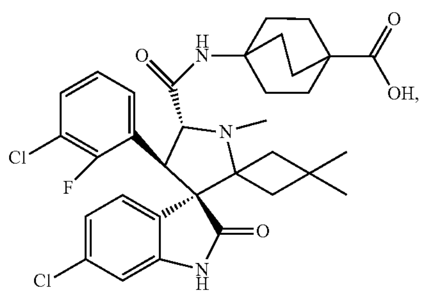

-continued

A12

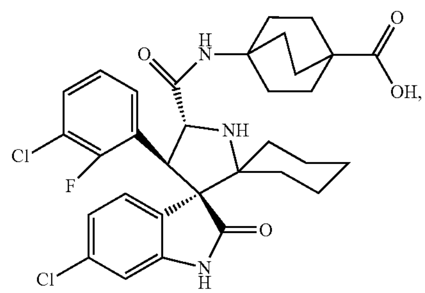

A13

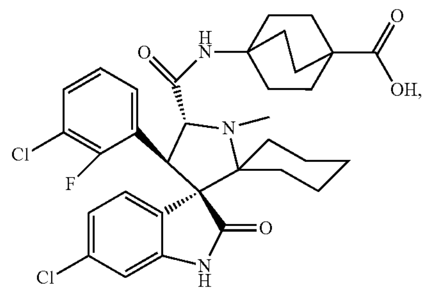

A14

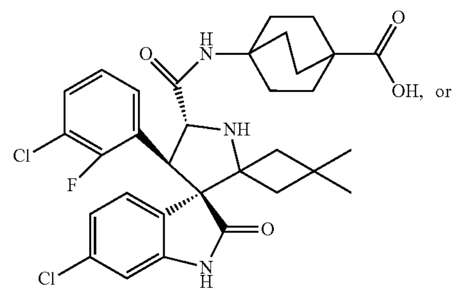

or

A15

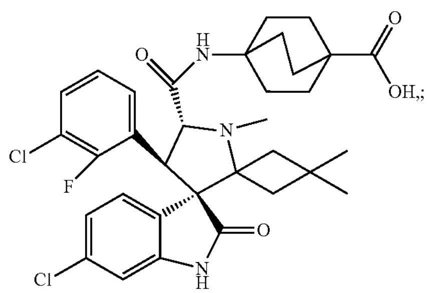

or a tautomer, a mixture of two or more tautomers, or an isotopic variant thereof; or a pharmaceutically acceptable salt, solvate, hydrate, or prodrug thereof.

In one embodiment, the MDM2 inhibitor provided herein is 3-((3'R,4'S,5'R)-6"-chloro-4'-(3-chloro-2-fluorophenyl)-2"-oxodispiro[cyclohexane-1,2'-pyrrolidine-3',3"-indoline]-5'-carboxamido)bicyclo[1.1.1]pentane-1-carboxylic acid A1, or a tautomer, a mixture of two or more tautomers, or an isotopic variant thereof; or a pharmaceutically acceptable salt, solvate, or hydrate thereof.

In another embodiment, the MDM2 inhibitor provided herein is 4-((3'R,4'S,5'R)-6"-chloro-4'-(3-chloro-2-fluorophenyl)-2"-oxodispiro[cyclohexane-1,2'-pyrrolidine-3',3"-indoline]-5'-carboxamido)bicyclo[2.2.2]octane-1-carboxylic acid A2, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S,5'R)-6"-chloro-4'-(3-chloro-2-fluorophenyl)-4,4-difluoro-2"-oxodispiro[cyclo-hexane-1,2'-pyrrolidine-3',3"-indoline]-5'-carboxamido)bicyclo[2.2.2]octane-1-carboxylic acid A3, or a tautomer, a mixture of two or more tautomers, or an isotopic variant thereof; or a pharmaceutically acceptable salt, solvate, or hydrate thereof.

In yet another embodiment, the MDM2 inhibitor provided herein is (3'R,4'S,5'R)-6"-chloro-4'-(3-chloro-2-fluorophenyl)-N-(4-((methylsulfonyl)carbamoyl)-bicyclo[2.2.2]octan-1-yl)-2"-oxodispiro[cyclohexane-1,2'-pyrrolidine-3',3"-indoline]-5'-carboxamide A4, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((1r,3'R,4R,4'S,5'R)-6"-chloro-4'-(3-chloro-2-fluorophenyl)-4-hydroxy-4-methyl-2"-oxodispiro[cyclohexane-1,2'-pyrrolidine-3',3"-indoline]-5'-carboxamido)-bicyclo[2.2.2]octane-1-carboxylic acid A5, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((1s,3'R,4R,4'S,5'R)-6"-chloro-4'-(3-chloro-2-fluorophenyl)-4-hydroxy-4-methyl-2"-oxodispiro[cyclohexane-1,2'-pyrrolidine-3',3"-indoline]-5'-carboxamido)-bicyclo[2.2.2]octane-1-carboxylic acid A6, or a tautomer, a mixture of two or more tautomers, or an isotopic variant thereof; or a pharmaceutically acceptable salt, solvate, or hydrate thereof.

In yet another embodiment, the MDM2 inhibitor provided herein is (3'R,4'S,5'R)—N-(4-carbamoylbicyclo[2.2.2]octan-1-yl)-6"-chloro-4'-(3-chloro-2-fluorophenyl)-1'-methyl-2"-oxodispiro[cyclohexane-1,2'-pyrrolidine-3',3"-indoline]-5'-carboxamide A7, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]octane-1-carboxylic acid A8, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S,5'R)-6"-chloro-4'-(3-chloro-2-fluorophenyl)-1'-methyl-2"-oxodispiro-[cyclohexane-1,2'-pyrrolidine-3',3"-indoline]-5'-carboxamido)bicyclo[2.2.2]octane-1-carboxylic acid A9, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S,5'R)-6"-chloro-4'-(3-chloro-2-fluorophenyl)-3,3-dimethyl-2"-oxodispiro[cyclobutane-1,2'-pyrrolidine-3',3"-indoline]-5'-carboxamido)bicyclo[2.2.2]octane-1-carboxylic acid A10, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S,5'R)-6"-chloro-4'-(3-chloro-2-fluorophenyl)-1',3,3-trimethyl-2"-oxodispiro[cyclobutane-1,2'-pyrrolidine-3',3"-indoline]-5'-carboxamido)bicyclo[2.2.2]octane-1-carboxylic acid A11, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S,5'R)-6"-chloro-4'-(3-chloro-2-fluorophenyl)-2"-oxo-1",2"-dihydrodispiro[cyclohexane-1,2'-pyrrolidine-3',3"-pyrrolo[3,2-c]pyridine]-5'-carboxamido)bicyclo[2.2.2]octane-1-carboxylic acid A12, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S,5'R)-6"-chloro-4'-(3-chloro-2-fluorophenyl)-1'-methyl-2"-oxo-1",2"-dihydrodispiro[cyclohexane-1,2'-pyrrolidine-3',3"-pyrrolo[3,2-c]pyridine]-5'-carboxamido)bicyclo[2.2.2]octane-1-carboxylic acid A13, or a tautomer, a mixture of two or more tautomers, or an isotopic variant thereof; or a pharmaceutically acceptable salt, solvate, or hydrate thereof.

In yet another embodiment, the MDM2 inhibitor provided herein is 4-((3'R,4'S,5'R)-6"-chloro-4'-(3-chloro-2-fluorophenyl)-3,3-dimethyl-2"-oxo-1",2"-dihydrodispiro[cyclobutane-1,2'-pyrrolidine-3',3"-pyrrolo[3,2-c]pyridine]-5'-carboxamido)bicyclo[2.2.2]octane-1-carboxylic acid A14, or a tautomer, a mixture of two or more tautomers, or an isotopic variant thereof; or a pharmaceutically acceptable salt, solvate, or hydrate thereof.

In still another embodiment, the MDM2 inhibitor provided herein is 4-((3'R,4'S,5'R)-6"-chloro-4'-(3-chloro-2-fluorophenyl)-1',3,3-trimethyl-2"-oxo-1",2"-dihydrodispiro[cyclobutane-1,2'-pyrrolidine-3',3"-pyrrolo[3,2-c]pyridine]-5'-carboxamido)bicyclo[2.2.2]octane-1-carboxylic acid A15, or a tautomer, a mixture of two or more tautomers, or an isotopic variant thereof; or a pharmaceutically acceptable salt, solvate, or hydrate thereof.

Additional MDM2 inhibitors can be found in U.S. Pat. No. 9,745,314, the disclosure of which is incorporated herein by reference in its entirety.

In certain embodiments, the MDM2 inhibitor provided herein is deuterium-enriched. In certain embodiments, the MDM2 inhibitor provided herein is carbon-13 enriched. In certain embodiments, the MDM2 inhibitor provided herein is carbon-14 enriched. In certain embodiments, the MDM2 inhibitor provided herein contains one or more less prevalent isotopes for other elements, including, but not limited to, $^{15}N$ for nitrogen; $^{17}O$ or $^{18}O$ for oxygen, and $^{33}S$, $^{34}S$, or $^{36}S$ for sulfur.

In certain embodiments, the MDM2 inhibitor provided herein has an isotopic enrichment factor of no less than about 5, no less than about 10, no less than about 20, no less than about 30, no less than about 40, no less than about 50, no less than about 60, no less than about 70, no less than about 80, no less than about 90, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when a compound at a given position is 100% enriched with the specified isotope. Thus, the maximum isotopic enrichment factor is different for different isotopes. The maximum isotopic enrichment factor is 6410 for deuterium and 90 for carbon-13.

In certain embodiments, the MDM2 inhibitor provided herein has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy.

In certain embodiments, the MDM2 inhibitor provided herein has a carbon-13 enrichment factor of no less than about 1.8 (about 2% carbon-13 enrichment), no less than about 4.5 (about 5% carbon-13 enrichment), no less than about 9 (about 10% carbon-13 enrichment), no less than about 18 (about 20% carbon-13 enrichment), no less than about 45 (about 50% carbon-13 enrichment), no less than about 68 (about 75% carbon-13 enrichment), no less than about 72 (about 80% carbon-13 enrichment), no less than about 77 (about 85% carbon-13 enrichment), no less than about 81 (about 90% carbon-13 enrichment), no less than about 86 (about 95% carbon-13 enrichment), no less than about 87 (about 97% carbon-13 enrichment), no less than about 88 (about 98% carbon-13 enrichment), no less than about 89 (about 99% carbon-13 enrichment), or no less than about 90 (about 99.5% carbon-13 enrichment). The carbon-13 enrichment can be determined using conventional analytical methods known to one of ordinary skill in the art, including mass spectrometry and nuclear magnetic resonance spectroscopy.

In certain embodiments, at least one of the atoms of the MDM2 inhibitor provided herein, as specified as isotopically enriched, has isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In any events, the isotopic enrichment of the isotopically enriched atom of the MDM2 inhibitor provided herein is no less than the natural abundance of the isotope specified.

In certain embodiments, at least one of the atoms of the MDM2 inhibitor provided herein, as specified as deuterium-enriched, has deuterium enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, at least one of the atoms of the MDM2 inhibitor provided herein, as specified as $^{3}C$-enriched, has carbon-13 enrichment of no less than about 2%, no less than about 5%, no less than about 10%, no less than about 20%, no less than about 50%, no less than about 70%, no less than about 80%, no less than about 90%, or no less than about 98%.

In certain embodiments, the MDM2 inhibitor provided herein is isolated or purified. In certain embodiments, the MDM2 inhibitor provided herein has a purity of at least about 80%, at least about 90%, at least about 95%, at least about 98%, at least about 99%, or at least about 99.5% by weight.

The MDM2 inhibitor provided herein is intended to encompass all possible stereoisomers, unless a particular stereochemistry is specified. Where the MDM2 inhibitor contains an alkenyl group, it may exist as one or mixture of geometric cis/trans (or Z/E) isomers. Where structural isomers are interconvertible, it may exist as a single tautomer or a mixture of tautomers. This can take the form of proton tautomerism in the MDM2 inhibitor that contains, for example, an imino, keto, or oxime group; or so-called valence tautomerism in the MDM2 inhibitor that contain an aromatic moiety. It follows that a single MDM2 inhibitor may exhibit more than one type of isomerism.

The MDM2 inhibitor provided herein can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a compound in its (R) form is equivalent, for the compound that undergoes epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the MDM2 inhibitor provided herein contains an acidic or basic moiety, it can also be provided as a pharmaceutically acceptable salt. See, e.g., Berge et al., *J. Pharm. Sci.* 1977, 66, 1-19; *Handbook of Pharmaceutical Salts: Properties, Selection, and Use,* 2nd ed.; Stahl and Wermuth Eds.; Wiley-VCH and VHCA, Zurich, 2011. In certain embodiments, a pharmaceutically acceptable salt of the MDM2 inhibitor provided herein is a solvate. In certain embodiments, a pharmaceutically acceptable salt of the MDM2 inhibitor provided herein is a hydrate.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

The MDM2 inhibitor provided herein may also be provided as a prodrug, which is a functional derivative of a compound, for example, of Formula (I) and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis.

Pharmaceutical Compositions

In one embodiment, provided herein is a microsuspension comprising: (i) microparticles of the MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; (ii) a surfactant; and (iii) a tonicity agent.

In another embodiment, provided herein is a microsuspension comprising: (i) microparticles of the MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof, in an amount ranging from about 0.1 to about 100 mg/mL; (ii) a surfactant in an amount ranging from about 0.001 to about 0.5% (w/v); and (iii) a tonicity agent in an amount ranging from about 0.6 to about 1.8% (w/v).

In yet another embodiment, provided herein is a microsuspension comprising: (i) microparticles of the MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof, in an amount of about 20 mg/mL; (ii) a surfactant in an amount of about 0.015% (w/v); and (iii) a tonicity agent in amount of about 0.9% (w/v).

In yet another embodiment, provided herein is a microsuspension comprising: (i) microparticles of the MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; (ii) a surfactant; (iii) a tonicity agent; and (iv) water.

In yet another embodiment, provided herein is a microsuspension comprising: (i) microparticles of the MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof, in an amount ranging from about 0.1 to about 100 mg/mL; (ii) a surfactant in an amount ranging from about 0.001 to about 0.5% (w/v); (iii) a tonicity agent in an amount ranging from about 0.6 to about 1.8% (w/v); and (iv) water.

In still another embodiment, provided herein is a microsuspension comprising: (i) microparticles of the MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof, in an amount of about 20 mg/mL; (ii) a surfactant in an amount of about 0.015% (w/v); and (iii) a tonicity agent in amount of about 0.9% (w/v); and (iv) water.

In certain embodiments, the microparticles have an average particle size ranging from about 1 μm to about 1,000 μm, from about 2 μm to about 500 μm, from about 5 μm to about 200 μm, from about 10 μm to about 100 μm, from about 10 μm to about 50 μm, or from about 10 μm to about 20 μm. In certain embodiments, the microparticles have an average particle size ranging from about 1 μm to about 1,000 μm. In certain embodiments, the microparticles have an average particle size ranging from about 2 μm to about 500 μm. In certain embodiments, the microparticles have an average particle size ranging from about 5 μm to about 200 μm. In certain embodiments, the microparticles have an average particle size ranging from about 10 μm to about 100 μm. In certain embodiments, the microparticles have an average particle size ranging from about 10 μm to about 50 μm. In certain embodiments, the microparticles have an average particle size ranging from about 10 μm to about 20 μm. In certain embodiments, the microparticles have an average particle size of about 10 μm, about 15 μm, about 20 μm, about 25 μm, about 30 μm, about 35 μm, about 40 μm, about 45 μm, or about 50 μm.

In certain embodiments, the microparticles have a D50 ranging from about 1 μm to about 1,000 μm, from about 2 μm to about 500 μm, from about 5 μm to about 200 μm, from about 10 μm to about 100 μm, from about 10 μm to about 50 μm, or from about 10 μm to about 20 μm. In certain embodiments, the microparticles have a D50 ranging from about 1 μm to about 1,000 μm. In certain embodiments, the microparticles have a D50 ranging from about 2 μm to about 500 μm. In certain embodiments, the microparticles have a D50 ranging from about 5 μm to about 200 μm. In certain embodiments, the microparticles have a D50 ranging from about 10 μm to about 100 μm. In certain embodiments, the microparticles have a D50 ranging from about 10 μm to about 50 μm. In certain embodiments, the microparticles have a D50 ranging from about 10 μm to about 20 μm. In certain embodiments, the microparticles have a D50 of about 10 μm, about 15 μm, about 20 μm, about 25 μm, about 30 μm, about 35 μm, about 40 μm, about 45 μm, or about 50 μm.

In certain embodiments, the microparticles have a D90 ranging from about 1 μm to about 2,000 μm, from about 2 μm to about 1,000 μm, from about 5 μm to about 500 μm, from about 10 μm to about 200 μm, from about 10 μm to about 100 μm, or from about 10 μm to about 50 μm. In certain embodiments, the microparticles have a D90 ranging from about 1 μm to about 2,000 μm. In certain embodiments, the microparticles have a D90 ranging from about 2 μm to about 1,000 μm. In certain embodiments, the microparticles have a D90 ranging from about 5 μm to about 500 μm. In certain embodiments, the microparticles have a D90 ranging from about 10 μm to about 200 μm. In certain embodiments, the microparticles have a D90 ranging from about 10 μm to about 100 μm. In certain embodiments, the microparticles have a D90 ranging from about 10 μm to about 50 μm. In certain embodiments, the microparticles have a D90 of about 10 μm, about 15 μm, about 20 μm, about 25 μm, about 30 μm, about 35 μm, about 40 μm, about 45 μm, about 50 μm, about 55 μm, or about 60 μm.

In certain embodiments, the microparticles have a D10 ranging from about 0.5 μm to about 200 μm, from about 1 μm to about 100 μm, from about 1 μm to about 50 μm, from about 1 μm to about 20 μm, from about 1 μm to about 10 μm, or from about 1 μm to about 5 μm. In certain embodiments, the microparticles have a D10 ranging from about 0.5 μm to about 200 μm. In certain embodiments, the microparticles have a D10 ranging from about 1 μm to about 100 μm. In certain embodiments, the microparticles have a D10 ranging from about 1 μm to about 50 μm. In certain embodiments, the microparticles have a D10 ranging from about 1 μm to about 20 μm. In certain embodiments, the microparticles have a D10 ranging from about 1 μm to about 10 μm. In certain embodiments, the microparticles have a D10 ranging from about 1 μm to about 5 μm. In certain embodiments, the microparticles have a D50 of about 1 μm, about 1.5 μm, about 2 μm, about 2.5 μm, about 3 μm, about 3.5 μm, about 4 μm, about 4.5 μm, or about 5 μm.

In certain embodiments, the microparticles are analyzed using a light scattering method.

In certain embodiments, the microsuspension provided herein comprises the MDM2 inhibitor at a concentration ranging from about 0.1 to about 1,000 mg/mL, from about 0.2 to about 500 mg/mL, from about 0.5 to about 200 mg/mL, from about 1 to about 100 mg/mL, from about 2 to about 50 mg/mL, or from about 5 to about 50 mg/mL. In certain embodiments, the microsuspension provided herein comprises the MDM2 inhibitor at a concentration ranging from about 0.1 to about 1,000 mg/mL. In certain embodiments, the microsuspension provided herein comprises the MDM2 inhibitor at a concentration ranging from about 0.2 to about 500 mg/mL. In certain embodiments, the microsuspension provided herein comprises the MDM2 inhibitor at a concentration ranging from about 0.5 to about 200 mg/mL. In certain embodiments, the microsuspension provided herein comprises the MDM2 inhibitor at a concentration ranging from about 1 to about 100 mg/mL. In certain embodiments, the microsuspension provided herein comprises the MDM2 inhibitor at a concentration ranging from about 2 to about 50 mg/mL. In certain embodiments, the microsuspension provided herein comprises the MDM2 inhibitor at a concentration ranging from about 5 to about 50 mg/mL. In certain embodiments, the microsuspension provided herein comprises the MDM2 inhibitor at a concentration of about 5, about 10, about 15, about 20, about 25, about 30, about 35, about 40, about 45, or about 50 mg/mL.

In certain embodiments, the surfactant is a nonionic surfactant. In certain embodiments, the surfactant is a polysorbate. In certain embodiments, the surfactant is polyoxyethylene (20) sorbitan monolaurate (TWEEN® 20), polyoxyethylene (20) sorbitan monopalmitate (TWEEN® 40), polyoxyethylene (20) sorbitan monostearate (TWEEN® 60), or polyoxyethylene (20) sorbitan monooleate (TWEEN® 80). In certain embodiments, the surfactant is polyoxyethylene (20) sorbitan monolaurate (TWEEN® 20). In certain embodiments, the surfactant is polyoxyethylene (20) sorbitan monopalmitate (TWEEN® 40). In certain embodiments, the surfactant is polyoxyethylene (20) sorbitan monostearate (TWEEN® 60). In certain embodiments, the surfactant is polyoxyethylene (20) sorbitan monooleate (TWEEN® 80).

In certain embodiments, the surfactant is a polyethoxylated castor oil or polyethoxylated hydrogenated castor oil. In certain embodiments, the surfactant is a PEG-40 hydrogenated castor oil (e.g., CREMOPHOR® RH40) or CREMOPHOR® EL. In certain embodiments, the surfactant is a poloxamer. In certain embodiments, the surfactant is PLURONIC® F68 or PLURONIC® F127. In certain embodiments, the surfactant is sorbitan trioleate (SPAN® 85), sorbitan monooleate (SPAN® 80), sorbitan monostearate (SPAN® 60), sorbitan monopalmitate (SPAN® 40), or sorbitan monolaurate (SPAN® 20).

In certain embodiments, the surfactant is an ionic surfactant. In certain embodiments, the surfactant is lecithin.

In certain embodiments, the microsuspension provided herein comprises the surfactant at a concentration ranging from about 0.001 to about 0.5% (w/v), from about 0.001 to about 0.2% (w/v), from about 0.002 to about 0.1% (w/v), from about 0.005 to about 0.05% (w/v), or from about 0.01 to about 0.02% (w/v). In certain embodiments, the microsuspension provided herein comprises the surfactant at a concentration ranging from about 0.001 to about 0.5% (w/v). In certain embodiments, the microsuspension provided herein comprises the surfactant at a concentration ranging from about 0.001 to about 0.2% (w/v). In certain embodiments, the microsuspension provided herein comprises the surfactant at a concentration ranging from about 0.002 to about 0.1% (w/v). In certain embodiments, the microsuspension provided herein comprises the surfactant at a concentration ranging from about 0.005 to about 0.05% (w/v). In certain embodiments, the microsuspension provided herein comprises the surfactant at a concentration ranging from about 0.01 to about 0.02% (w/v). In certain embodiments, the microsuspension provided herein comprises the surfactant at a concentration of about 0.005, about 0.007, about 0.01, about 0.012, about 0.015, about 0.017, about 0.02, about 0.022, about 0.025, about 0.03, about 0.04, or about 0.05% (w/v).

In certain embodiments, the tonicity agent is dextrose, glycerin, or sodium chloride. In certain embodiments, the tonicity agent is dextrose. In certain embodiments, the tonicity agent is glycerin. In certain embodiments, the tonicity agent is sodium chloride.

In certain embodiments, the microsuspension provided herein comprises the tonicity agent at a concentration ranging from about 0.6 to about 1.8% (w/v), from about 0.6 to about 1.5% (w/v), or from about 0.6 to about 1.2% (w/v). In certain embodiments, the microsuspension provided herein comprises the tonicity agent at a concentration ranging from about 0.6 to about 1.8% (w/v). In certain embodiments, the microsuspension provided herein comprises the tonicity agent at a concentration ranging from about 0.6 to about 1.5% (w/v). In certain embodiments, the microsuspension provided herein comprises the tonicity agent at a concentration ranging from about 0.6 to about 1.2% (w/v). In certain embodiments, the microsuspension provided herein comprises the tonicity agent at a concentration of about 0.6, about 0.7, about 0.8, about 0.9, about 1, about 1.1, about 1.2, about 1.3, about 1.4, about 1.5, about 1.6, about 1.7, or about 1.8% (w/v).

In certain embodiments, the microsuspension provided herein has an osmolality ranging from about 200 to about 600 mOsm/L, from about 220 to about 400 mOsm/L, or from about 250 to about 300 mOsm/L. In certain embodiments, the microsuspension provided herein has an osmolality ranging from about 200 to about 600 mOsm/L. In certain embodiments, the microsuspension provided herein has an osmolality ranging from about 220 to about 400 mOsm/L. In certain embodiments, the microsuspension provided herein has an osmolality ranging from about 250 to about 300 mOsm/L. In certain embodiments, the microsuspension provided herein has an osmolality of about 250, about 255, about 260, about 265, about 270, about 275, about 280, about 285, about 290, about 295, or about 300 mOsm/L.

In certain embodiments, the microsuspension provided herein has a pH ranging from about 5 to about 8, from about 5.5 to about 8, from about 6.5 to about 8, or from about 6 to about 8. In certain embodiments, the microsuspension provided herein has a pH ranging from about 5 to about 8. In certain embodiments, the microsuspension provided herein has a pH ranging from about 5.5 to about 8. In certain embodiments, the microsuspension provided herein has a pH ranging from about 6.5 to about 8. In certain embodiments, the microsuspension provided herein has a pH ranging from about 6 to about 8. In certain embodiments, the microsuspension provided herein has a pH of about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, or about 8. In certain embodiments, the microsuspension provided herein has a pH of about 6.5, about 6.6, about 6.7, about 6.8, about 6.9, about 7, about 7.1, about 7.2, about 7.3, about 7.4, about 7.5, about 7.6, about 7.7, about 7.8, about 7.9, or about 8. In certain embodiments, the microsuspension provided herein has a pH of about 6.5, about 6.6, about 6.7, about 6.8, about 6.9, about 7, about 7.1, about 7.2, about 7.3, about 7.4, or about 7.5.

In one embodiment, provided herein is a microsuspension comprising: (i) microparticles of 4-((3'R,4'S,5'R)-6"-chloro- 4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof; (ii) a surfactant; and (iii) a tonicity agent.

In another embodiment, provided herein is a microsuspension comprising: (i) microparticles of 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof, in an amount ranging from about 0.1 to about 100 mg/mL; (ii) a surfactant in an amount ranging from about 0.001 to about 0.5% (w/v); and (iii) a tonicity agent in an amount ranging from about 0.6 to about 1.8% (w/v).

In yet another embodiment, provided herein is a microsuspension comprising: (i) microparticles of 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof, in an amount of about 20 mg/mL; (ii) a surfactant in an amount of about 0.015% (w/v); and (iii) a tonicity agent in an amount of about 0.9% (w/v).

In yet another embodiment, provided herein is a microsuspension comprising: (i) microparticles of 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof; (ii) a surfactant; (iii) a tonicity agent; and (iv) water.

In yet another embodiment, provided herein is a microsuspension comprising: (i) microparticles of 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof, in an amount ranging from about 0.1 to about 100 mg/mL; (ii) a surfactant in an amount ranging from about 0.001 to about 0.5% (w/v); (iii) a tonicity agent in an amount ranging from about 0.6 to about 1.8% (w/v); and (iv) water.

In yet another embodiment, provided herein is a microsuspension comprising: (i) microparticles of 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof, in an amount of about 20 mg/mL; (ii) a surfactant in an amount of about 0.015% (w/v); (iii) a tonicity agent in an amount of about 0.9% (w/v); and (iv) water.

In one embodiment, provided herein is a microsuspension comprising: (i) microparticles of 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof; (ii) polyoxyethylene (20) sorbitan monooleate; and (iii) sodium chloride.

In another embodiment, provided herein is a microsuspension comprising: (i) microparticles of 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof, in an amount ranging from about 0.1 to about 100 mg/mL; (ii) polyoxyethylene (20) sorbitan monooleate in an amount ranging from about 0.001 to about 0.5% (w/v); and (iii) sodium chloride in an amount ranging from about 0.6 to about 1.8% (w/v).

In yet another embodiment, provided herein is a microsuspension comprising: (i) microparticles of 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof, in an amount of about 20 mg/mL; (ii) polyoxyethylene (20) sorbitan monooleate in an amount of about 0.015% (w/v); and (iii) sodium chloride in an amount of about 0.9% (w/v).

In yet another embodiment, provided herein is a microsuspension comprising: (i) microparticles of 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof; (ii) polyoxyethylene (20) sorbitan monooleate; (iii) sodium chloride; and (iv) water.

In yet another embodiment, provided herein is a microsuspension comprising: (i) microparticles of 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof, in an amount ranging from about 0.1 to about 100 mg/mL; (ii) polyoxyethylene (20) sorbitan monooleate in an amount ranging from about 0.001 to about 0.5% (w/v); (iii) sodium chloride in an amount ranging from about 0.6 to about 1.8% (w/v); and (iv) water.

In still another embodiment, provided herein is a microsuspension comprising: (i) microparticles of 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof, in an amount of about 20 mg/mL; (ii) polyoxyethylene (20) sorbitan monooleate in an amount of about 0.015% (w/v); (iii) sodium chloride in an amount of about 0.9% (w/v); and (iv) water.

In one embodiment, provided herein is a microsuspension comprising: (i) microparticles of the MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; (ii) polyoxyethylene (20) sorbitan monooleate; and (iii) sodium chloride.

In another embodiment, provided herein is a microsuspension comprising: (i) microparticles of the MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof, in an amount ranging from about 0.1 to about 100 mg/mL; (ii) polyoxyethylene (20) sorbitan monooleate in an amount ranging from about 0.001 to about 0.5% (w/v); and (iii) sodium chloride in an amount ranging from about 0.6 to about 1.8% (w/v).

In yet another embodiment, provided herein is a microsuspension comprising: (i) microparticles of the MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof, in an amount of about 20 mg/mL; (ii) polyoxyethylene (20) sorbitan monooleate in an amount of about 0.015% (w/v); and (iii) sodium chloride in an amount of about 0.9% (w/v).

In yet another embodiment, provided herein is a microsuspension comprising: (i) microparticles of the MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof; (ii) polyoxyethylene (20) sorbitan monooleate; (iii) sodium chloride; and (iv) water.

In yet another embodiment, provided herein is a microsuspension comprising: (i) microparticles of the MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof, in an amount ranging from about 0.1 to about 100 mg/mL; (ii) polyoxyethylene (20) sorbitan monooleate in an amount ranging from about 0.001 to about 0.5% (w/v); (iii) sodium chloride in an amount ranging from about 0.6 to about 1.8% (w/v); and (iv) water.

In still another embodiment, provided herein is a microsuspension comprising: (i) microparticles of the MDM2 inhibitor of Formula (I), or a diastereomer, a mixture of two or more diastereomers, a tautomer, a mixture of two or more tautomers, or an isotopic variant thereof; or a pharmaceutically acceptable salt, solvate, hydrate, or prodrug thereof, in an amount of about 20 mg/mL; (ii) polyoxyethylene (20) sorbitan monooleate in an amount of about 0.015% (w/v); (iii) sodium chloride in an amount of about 0.9% (w/v); and (iv) water.

In one embodiment, the microsuspension is provided for ocular application. In another embodiment, the microsuspension is provided for intravitreal administration.

In one embodiment, the microsuspension is provided for ocular application. In another embodiment, the microsuspension is provided for intravitreal administration.

In certain embodiments, the microsuspension is sterilized. In certain embodiments, the microsuspension is isotonic. In certain embodiments, the microsuspension is isosmotic.

The MDM2 inhibitor-containing microsuspension can also be formulated as modified release dosage forms, including delayed-, extended-, prolonged-, sustained-, pulsatile-, controlled-, accelerated-, fast-, targeted-, and programmed-release dosage forms. These dosage forms can be prepared according to conventional methods and techniques known to those skilled in the art. See, e.g., *Remington: The Science and Practice of Pharmacy*, supra; *Modified-Release Drug Delivery Technology,* 2nd Edition, Rathbone et al., Eds., Marcel Dekker, Inc.: New York, NY, 2008.

The MDM2 inhibitor-containing microsuspension can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule and syringe. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial or bottle of pints or gallons.

Methods of Use

In one embodiment, provided herein is a method of treating, preventing, or alleviating an MDM2-mediated disorder, disease, or condition in a subject, comprising administering to the subject in need thereof a therapeutically effective amount of an microsuspension provided herein.

In certain embodiments, the MDM2-mediated disorder, disease, or condition is a retinal disease, age-related macular degeneration (AMD), diabetic retinopathy, retinal vein occlusions, glaucoma, retinoblastoma, and uveal melanoma.

In one embodiment, the MDM2 is a human MDM2, which is also known as HDM2.

In certain embodiments, the subject is a mammal. In certain embodiments, the subject is a human.

In certain embodiments, the microsuspension provided herein is administered parenterally. In certain embodiments, the microsuspension provided herein is administered parenterally. In certain embodiments, the microsuspension provided herein is administered intravitreally.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: mg (milligrams); mL (milliliters); μL (microliters); μm (micrometers); nm (nanometers); mM (millimolar); μM (micromolar); h (hour or hours); and min (minutes).

Example 1

Preparation of Microsuspension Formulation 1

Amorphous particles of compound A8 were dispersed into 0.015% TWEEN® 80 in a saline (w/v) at the concentration of 20 mg/mL to form a mixture. The mixture was milled by a mortar and pestle under sterilized conditions to form microsuspension 1 with a pH of 7.6. As shown in FIG. 1, microsuspension 1 was determined to have a D90 around 27 μm, which readily passed through a 30 G needle syringe. The final concentration of compound A8 in microsuspension 1 was about 20 mg/mL as determined by HPLC.

TABLE 1

| Particle Size Parameters | | | | | |
|---|---|---|---|---|---|
| | MV (μm) | SD | D10 (μm) | D50 (μm) | D90 (μm) |
| Microsuspension 1 | 14.0 | 10.3 | 2.8 | 12.6 | 27.4 |

Example 2

Preparation of Nanosuspension Formulation 2

Figure 2:
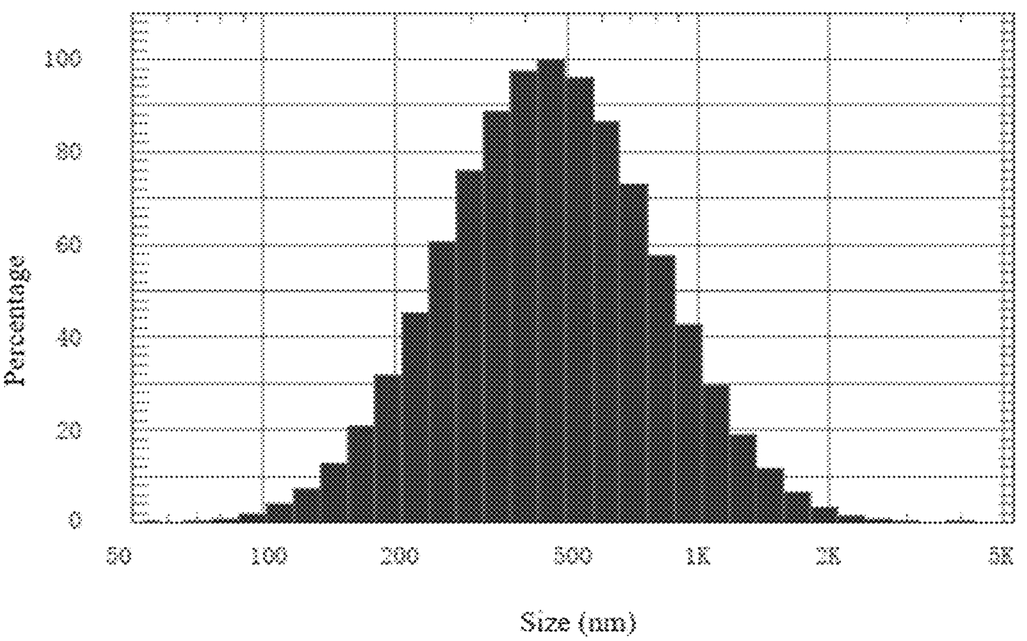
FIG. 2 shows the particle size distribution of nanosuspension 2.

Amorphous particles of compound A8 were dispersed into 0.5% HPMC E5 and 0.5% TWEEN® 80 in a 20 mM (pH 7.4) phosphate buffered saline (w/v) at the concentration of 40 mg/mL to obtain a homogenous suspension. The suspension was milled using a roller mixer 755 RMV (Stonewear, USA) at 200 rpm with 0.5 mm beads to obtain nanosuspension 2 with a pH of 7.4. As shown in FIG. 2, nanosuspension 2 was determined to have a D25 around 310 nm, a D50 around 453 nm, a D75 around 662, and a D90 around 930 nm, which readily passed through a 31G needle syringe. The final concentration of compound A8 in nanosuspension 2 was about 27 mg/mL as determined by HPLC.

Example 3

Preparation of Solution Formulation 3

Amorphous particles of compound A8 were dispersed into 5% PLURONIC® F68 in a 10 mM (pH 7.4) phosphate buffered saline (w/v) to form a mixture. The mixture was stirred overnight to obtain a slightly turbid solution and then filtrated through 0.22 μm membrane to obtain solution 3 with a pH of 7.4, which was stored in a sterile vial until use. The final concentration of compound A8 in solution 3 was about 3 mg/mL as determined by HPLC.

Example 4

Ocular Toxicity Study of Formulations after Intravitreal Injection

Cyno monkeys were intravitreally injected with formulations of compound A8. Two to three days after injection, ocular toxicity was evaluated by a slit-lamp, and any abnormal findings in pupil, cornea, anterior chamber, lens, vitreous body, and fundus were recorded and summarized in Table 2.

Solution 3, which contained PLURONIC® F68 as a solubilizing agent, showed severe ocular toxicity at the dose of 0.3 mg/eye. The pupil showed no response to light and was unable to dilate. Neovascularization, edema, and opacity were observed in cornea. In the anterior chamber, uniform gray granules and fibrous exudate were observed. Lens, vitreous body, and fundus were not visible under the slit-lamp. It was likely the high amount of solubilizing agent (5% PLURONIC® F68) or the high concentration of compound A8 is responsible for the severe toxicity.

Nanosuspension 2 showed slightly less severe ocular toxicity. At both dose levels of 0.5 mg/eye and 0.1 mg/eye, cornea and fundus were not affected. Pupil showed reduced sensitivity to light and was unable to dilate completely. The vitreous body was not visible due to inflammation.

On the other hand, microsuspension 1 was much less toxic than solution 3 and nanosuspension 2 even at a higher dose. At the dose of 1 mg/eye, microsuspension 1 did not affect the pupil, cornea, and fundus. It only caused slight inflammation in the anterior chamber and lens. The uniform gray granules in anterior vitreous body could be the injected drug particles.

Lastly, when CMC-Na, a commonly use suspending agent, was incorporated into microsuspension 1 at the same dose of 1 mg/eye, ocular toxicity was observed as reflected by invisible lens, vitreous body and fundus. In addition, the pupil showed no response to light and was unable to dilate.

TABLE 2

| Evaluation of Ocular Toxicity of Formulations | | | | | | |
|---|---|---|---|---|---|---|
| | Microsuspension | | Microsuspension (CMC-Na) | Nanosuspension | | Solution |
| Dose | 1 mg/eye | 0.2 mg/eye | 1 mg/eye | 0.5 mg/eye | 0.1 mg/eye | 0.3 mg/eye |
| Observation | Day 3 post injection | | Day 2 post injection | Day 2 post injection | | Day 2 post injection |
| Pupil | | | No response to light; unable to dilate | Reduced sensitivity to light; unable to completely dilate | Reduced sensitivity to light; unable to completely dilate | No response to light; unable to dilate |
| Cornea | | | | | | Neovascularization; edema; opacity |
| Anterior Chamber | Uniform gray granules; flare | Uniform gray granules; flare | Uniform gray granules; fibrous exudate | Uniform gray granules; flare | Uniform gray granules; flare; fibrous exudate | Uniform gray granules; fibrous exudate |
| Lens | Posterior lens capsule opacity; gray dotted attachment | Posterior lens capsule opacity | Invisible | Posterior lens capsule opacity | | Invisible |
| Vitreous body | Uniform gray | Uniform gray | Invisible | Invisible | Invisible | Invisible |

TABLE 2-continued

| Evaluation of Ocular Toxicity of Formulations | | | | | |
|---|---|---|---|---|---|
| | Microsuspension | | Microsuspension (CMC-Na) | Nanosuspension | Solution |
| | granules in anterior vitreous body | granules in anterior vitreous body | | | |
| Fundus | | | Invisible | | Invisible |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A microsuspension comprising (i) microparticles of a MDM2 inhibitor; (ii) a surfactant; and (iii) a tonicity agent; wherein the MDM2 inhibitor is 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]octane-1-carboxylic acid A8, or a tautomer, a mixture of two or more tautomers, or an isotopic variant thereof; or a pharmaceutically acceptable salt, solvate, or hydrate thereof, wherein the surfactant is a polysorbate, a polyethoxylated castor oil, a polyethoxylated hydrogenated castor oil, a poloxamer, sorbitan trioleate, sorbitan monooleate, sorbitan monostearate, sorbitan monopalmitate, sorbitan monolaurate, or lecithin, wherein the surfactant has a concentration ranging from about 0.001 to about 0.04% (w/v), and wherein the tonicity agent is dextrose, glycerin, or sodium chloride.

2. The microsuspension of claim 1, comprising the MDM2 inhibitor at a concentration ranging from about 0.1 to about 1,000 mg/mL, or from about 5 to about 50 mg/mL.

3. The microsuspension of claim 1, comprising the MDM2 inhibitor at a concentration of about 5, about 10, about 15, about 20, about 25, about 30, about 35, about 40, about 45, or about 50 mg/mL.

4. The microsuspension of claim 1, wherein the surfactant is a polysorbate.

5. The microsuspension of claim 1, wherein the surfactant is polyoxyethylene (20) sorbitan monolaurate, polyoxyethylene (20) sorbitan monopalmitate, polyoxyethylene (20) sorbitan monostearate, or polyoxyethylene (20) sorbitan monooleate.

6. The microsuspension of claim 5, wherein the surfactant is polyoxyethylene (20) sorbitan monooleate.

7. The microsuspension of claim 1, comprising the surfactant at a concentration of about 0.005, about 0.007, about 0.01, about 0.012, about 0.015, about 0.017, about 0.02, about 0.022, about 0.025, about 0.03, or about 0.04, or about 0.05% (w/v).

8. The microsuspension of claim 1, wherein the tonicity agent is sodium chloride.

9. The microsuspension of claim 1, comprising the tonicity agent at a concentration ranging from about 0.6 to about 1.8% (w/v), or from about 0.6 to about 1.2% (w/v).

10. The microsuspension claim 9, comprising the tonicity agent at a concentration of about 0.6, about 0.7, about 0.8, about 0.9, about 1, about 1.1, about 1.2, about 1.3, about 1.4, about 1.5, about 1.6, about 1.7, or about 1.8% (w/v).

11. The microsuspension of claim 1, comprising: (i) microparticles of 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof, in an amount of about 0.1 to about 100 mg/mL; (ii) polyoxyethylene (20) sorbitan monooleate, in an amount of about 0.001 to about 0.04% (w/v); and (iii) sodium chloride in an amount of about 0.6 to about 1.8% (w/v).

12. The microsuspension of claim 11, comprising: (i) microparticles of 4-((3'R,4'S,5'R)-6"-chloro-4'-(3-chloro-2-fluorophenyl)-1'-ethyl-2"-oxodispiro-[cyclohexane-1,2'-pyrrolidine-3',3"-indoline]-5'-carboxamido)bicyclo[2.2.2]-octane-1-carboxylic acid A8, or a tautomer, a mixture of two or more tautomers, or an isotopic variant thereof; or a pharmaceutically acceptable salt, solvate, or hydrate thereof, in an amount of about 20 mg/ml; (ii) polyoxyethylene (20) sorbitan monooleate in an amount of about 0.015% (w/v); and (iii) sodium chloride in an amount of about 0.9% (w/v).

13. The microsuspension of claim 1, further comprising water.

14. The microsuspension of claim 1, wherein the microsuspension has an osmolality ranging from about 200 to about 600 mOsm/L, or from about 250 to about 300 mOsm/L.

15. The microsuspension of claim 14, wherein the microsuspension has an osmolality of about 250, about 255, about 260, about 265, about 270, about 275, about 280, about 285, about 290, about 295, or about 300 mOsm/L.

16. The microsuspension of claim 1, wherein the microsuspension has a pH ranging from about 5 to about 8, from about 6 to about 7.5, about 6.5, about 6.6, about 6.7, about 6.8, about 6.9, about 7, about 7.1, about 7.2, about 7.3, about 7.4, or about 7.5.

17. A method of treating, preventing, or alleviating one or more symptoms of a disorder, disease, or condition mediated by an MDM2 in a subject, comprising administering to the subject in need thereof a therapeutically effective amount of the microsuspension of claim 1, wherein the disorder, disease, or condition is an ocular disease.

18. The method of claim 17, wherein an ocular disease is a retinal disease, age-related macular degeneration (AMD), diabetic retinopathy, retinal vein occlusions, glaucoma, retinoblastoma, or uveal melanoma.

* * * * *